United States Patent
Marchand et al.

(10) Patent No.: US 6,959,270 B2
(45) Date of Patent: Oct. 25, 2005

(54) METHOD FOR MODELING THE TRANSPORT OF IONS IN HYDRATED CEMENT SYSTEMS

(75) Inventors: Jacques Marchand, Sillery (CA); Eric Samson, Quebec (CA); Yannick Maltais, Sainte-Foy (CA)

(73) Assignees: Université Laval, Québec (CA); SIMCO Technologies Inc., Québec (CA)

( * ) Notice: Subject to any disclaimer, the term of this patent is extended or adjusted under 35 U.S.C. 154(b) by 718 days.

(21) Appl. No.: 09/863,904

(22) Filed: May 24, 2001

(65) Prior Publication Data

US 2003/0040892 A1 Feb. 27, 2003

(51) Int. Cl.[7] .............................. G06G 7/48; G06G 7/58
(52) U.S. Cl. ................................. 703/12; 703/2; 703/6; 702/22; 106/640; 106/713; 106/772
(58) Field of Search .............................. 703/1–2, 6–12; 702/22–32; 106/640, 713, 772

(56) References Cited

U.S. PATENT DOCUMENTS 6,217,742 B1 * 4/2001 Bennett ...................... 205/734
6,398,945 B1 * 6/2002 Henriksen ................... 205/734

OTHER PUBLICATIONS

Truc et al, "Numerical Simulation of Multi–Species Transport Through Saturated Concrete During a Migration Test—MsDiff Code," Cement and Concrete Research, vol. 30 No. 10, pp. 1518–1592 (Oct. 2000).*

Li et al, "Finite Element Modelling of Chloride Removal from Concrete by an Electrochemical Method," Corrosion Science, vol. 42 No. 12, pp. 2145–2165 (Sep. 2000).*

Studies on the Stability of Calcium Chloraluminate, M. Ben–Yair, Israel Journal of Chemistry, vol. 9, 1971, pp. 529–536.

Prediction and Field Verification of Subsurface–Water Quality Changes During Artificial Recharge, D.B. Grove, W.W. Wood, Ground Water, vol. 17, No. 3, 1979 pp. 250–257.

Étude Fondamentale Des Transferts Couples ChaleurMasse En Milieu Poreux, P.Crausse, G. Bacon, S. Bories, Int. J. Heat Mass Transfer, vol. 24, No. 6, pp. 991–1004 1981.

(Continued)

*Primary Examiner*—Samuel Broda, Esq.
(74) *Attorney, Agent, or Firm*—Ogilvy Renault, LLP; Isabelle Chabot

(57) ABSTRACT

The present invention relates to a computational tool that allows to evaluate the degradation of cement-based materials under various types of chemical attacks such as sulfates, chlorides, and plain water. It is based on the physical principles of ionic mass conservation and chemical equilibrium between a solution and different solid phases. The effect of the dissolution or the precipitation of solid phases on the transport coefficients is considered. A method for determining an ion concentration in solution of at least two ions capable of undergoing transport in a cement-based material under a chemical attack and a solid phase profile for at least one component of said cement-based material is provided. A method for determining a diffusion coefficient for each of at least two ions capable of undergoing transport in a cement-based material is also provided.

20 Claims, 12 Drawing Sheets

OTHER PUBLICATIONS

Transport of Reacting Solutes in Porous Media; Relation Between Mathematical Nature of Problem Formulation and Chemical Nature of Reactions, J. Rubin Water Resources Research, vol. 19, No. 5, pp. 1231–1252, 1983.

Condensation and Isothermal Water Transfer in Cement Mortar Part I—Pore Size Distribution, Equlibrium Water Condensation and Imbibition, J.–F. Dalan, Transport in Porous Media 3, pp. 563–589, 1988.

An Ion Interaction Model for the Determination of Chemical Equilibria in Cement/Water Systems, E.J. Reardon, Research, vol. 20, pp. 175–192, 1990.

Computer Simulation of the Diffusivity of Cement–Based Materials, E.J. Garboczi, D.P. Bentz, Journal of Materials Science, vol. 27, pp. 2083–2092, 1992.

Chloride Binding Capacity and Binding Isothermas of OPC Pastes and Mortars, L. Tang, L–O Nilsson, Cement and Concrete Research, vol. 23, pp. 247–253, 1993.

Thermodynamic Investigation of the $CaO-Al_2O_3-CaSO_4-H_2O$ System at 25° C. and the Influence of $Na_2O$, D. Damidot, F.P. Glasser, Cement and Concrete Research, vol. 23, No. 1, pp. 221–238, 1993.

Aqueous Phase Equilibria in the System $CaO-Al_2O_3-CaCl_2-H_2O$: The Significance and Stability of Friedel's Salt, C. Abate, B.E. Scheetz, Journal of the American Ceramic Society, vol. 78, No. 4, pp. 939–944, 1995.

Thermodynamic Investigation of the $CaO-Al_2O_3-CaSO_4-K_2O-H_2O$ System at 25° C., D. Damidot, F.P. Glasser, Cement and Concrete Research, vol. 23, No. 5, pp. 1195–1204, 1993.

Analysis of Chloride Diffusion into Partially Saturated Concrete, A.V. Saetta, R.V. Scotta, R.V. Vitaliani, ACI Materials Journal, vol. 90, No. 5, pp. 441–451, 1993.

Calculation of Chloride Diffusion Coefficients in Concrete from Ionic Migration Measurements, C. Andrade, Cement and Concrete Research, vol. 23, pp. 724–742, 1993.

Moisture Diffusion in Cementitious Materials, Adsorption Isotherms, Y. Xi, ZP Bazant, H.M. Jennings, Advance Cement Based Materials, vol. 1, pp. 248–257, 1994.

Moisture Transport in Porous Building Materials, L. Pel. Eindhoven University of Technology, Netherlands, Ph.D. Thesis, pp. 1–127, 1994.

Barrier Performance of Concrete: A Review of Fluid Transport Theory, C. Hall, Materials and Structures, vol. 27, pp. 291–308, 1994.

Diffusion Behavior of Chloride Ions in Concrete, T. Zhang, O.E. Gjorv, Cement and Concrete Research, vol. 26, No. 6, pp. 907–917, 1996.

Numerical Simulation of Reinforced Concrete Deterioration–Part I: Chloride Diffusion, E.J. Hansen, V.E. Saouma, ACI Material Journal, vol. 96, No. 2, pp. 173–180, 1999.

Diffusion of Sulfate Ions Into Cement Stone Regarding Simultaneous Chemical Reactions and Resulting Effects, P.N. Gospodinov. R.F. Kazandjev, T.A. Partalin, M.K. Mironova, Cement and Concrete Research, vol. 29, pp. 1591–1596, 1999.

Influence of Voltage on Chloride Diffusion Coefficients From Chloride Migration Tests, P.F. McGrath, R.D. Hooton, Cement and Concrete Research, vol. 26, No. 8, pp. 1239–1244, 1996.

Simulation of Chloride Penetration in Cement–Based Materials, M. Masi, D. Colella, G. Radaelli, L. Bertolini, Cement and Concrete Research, vol. 27, No. 10, pp. 1591–1601, 1997.

Modelling of Electrochemical Chloride Extraction From Concrete: Influence of Ionic Activity Coefficients, L.Y. Li, C.L. Page, Computational Materials Science, vol. 9, pp. 303–308, 1998.

Modeling of Chloride Diffusion in Concrete and Determination of Diffusion Coefficients, M. Nagesh, B. Bhattacharjee, ACI Materials Journal, vol. 95, No. 2, pp. 113–120, 1998.

Étude Des Mécaniques De Transport De L'eau Par Absorption Capillaire Dans Des Matériaux Cimentaires Usuels Et De Haute Performance, K, Hazrati, Ph.D. Thesis, Laval University, Canada, 1998.

Service Life Modelling of R.C. Highway Structures Exposed to Chlorides, B. Martin–Pérez, Ph.D. Thesis, Toronto University, Canada, 1996.

Describing Ion Diffusion Mechanisms in Cement–Based Materials Using the Homogenization Technique, E. Samson, J. Marchand, J.J. Beaudoin, Cement and Concrete Research, vol. 29, No. 8, pp. 1341–1345, 1999.

Modeling Chemical Activity Effects in Strong Ionic Solutions, E. Samson, G. Lemaine, J. Marchand, J.J. Beaudoin, Computational Materials Science, vol. 15, No. 3, pp. 285–295, 1999.

Modelling Ion Diffusion Mechanisms in Porous Media, E. Samson, J. Marchand, J.L. Robert, J.P. Borunazel, International Journal for Numerical Methods in Engineering, vol. 46, pp. 2043–2060, 1999.

Numerical Solution of the Extended Nernst–Planck Model, E. Samson, J. Marchand, Journal of Colloid and Interface Science, vol. 215, pp. 1–8, 1999.

New Algorithms for Modeling Dissolution/Precipitation Reactions in Cement–Based Materials, E. Samson, J. Marchand, pp. 1–31, Submitted 2000.

A New Way for Determining the Chloride Diffusion Coefficient in Concrete from Steady State Migration Test, O. Truc. J.P.125 Ollivier, M. Carcassès, Cement and Concrete Research, vol. 30. pp. 217–226, 2000.

Chloride Ingress in Partially and Fully Saturated Concretes. S. Swaddiwudhipong, S.F. Wong, T.H. Wee, S.L. Lee, Concrete Science and Engineering, vol. 2, pp. 17–31, 2000.

Numerical Simulation of Multi–Species Diffusion, O. Truc. J.P. Ollivier, L.O. Nilsson, Materials and Structures, vol. 33, pp. 566–573, 2000.

The Solubility of Ettringgite at 25° C., C.J. Warren, E.J. Reardon, Cement and Concrete Research, vol. 24, No. 8, pp. 1515–1524, 1994.

Rapid Determination of the Chloride Diffusivity in Concrete by Applying an Electrical Field, T. Luping, L.O. Nilsson, ACI Materials Journal, vol. 89, No. 1, pp. 49–53, 1992.

Simultaneous Heat, Mass, and Momentum Transfer in Porous Media: A Theory of Drying, S. Whitaker, Advances in Heat Transfer, vol. 13, pp. 119–203, 1977.

Physical Structure of Hardened Cement Paste. A Classical Approach, Matériaux et Constructions, vol. 19, No. 114, pp. 423–436.

An Electrochemical Method for Accelerated Testing of Chloride Diffusivity in Concrete, T. Zhang, O.D. Gjorg, Cement and Concrete Research, Vo. 24, No. 8, pp. 1534–1548, 1994.

* cited by examiner

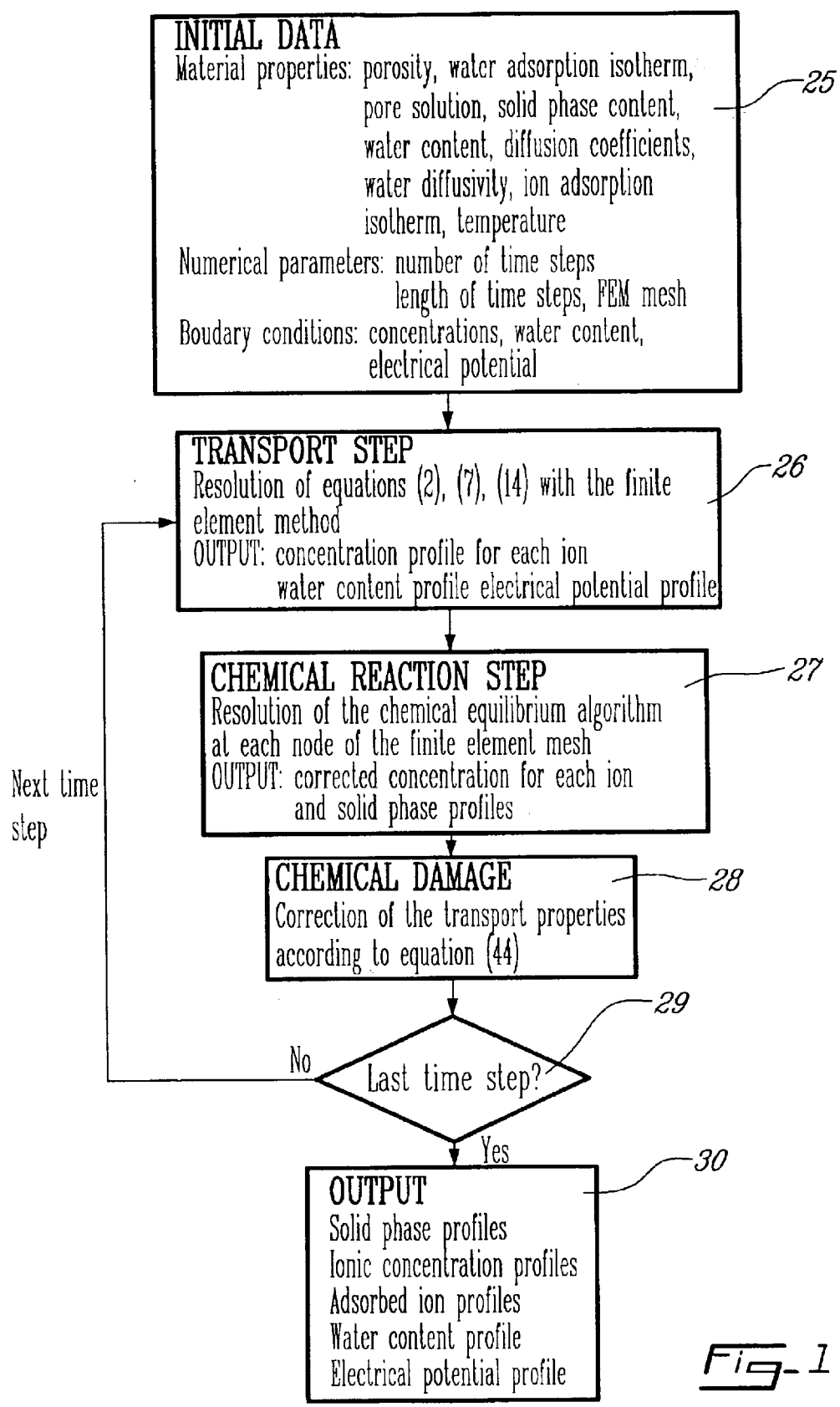

METHOD FOR MODELING THE TRANSPORT OF IONS IN HYDRATED CEMENT SYSTEMS

FIELD OF THE INVENTION

The present invention relates to a computational tool that allows to evaluate the degradation of cement-based materials under various types of chemical attacks such as sulfates, chlorides, and plain water. It is based on the physical principles of ionic mass conservation and chemical equilibrium between a solution and different solid phases. The effect of the dissolution or the precipitation of solid phases on the transport coefficients is considered. The transport equations are discretized in a computer code using the finite element method (FEM).

BACKGROUND OF THE INVENTION

The degradation of concrete structures under the effect of chemical attacks has become a major concern for civil engineers. The most common examples of chemical attacks are the corrosion of reinforcement bars as a result of chloride exposure, external sulfate attacks, carbonation and alcaliaggregate reactions. For the corrosion case, the cost of repair of the concrete structures exposed to this problem is estimated at 20 billion dollars in the U.S. only.

All of these examples of premature concrete structure degradations have their origin in ionic exchanges between the material and its environment. The corrosion of reinforcement bars is caused mainly by the penetration of external chloride in the concrete porous network. The presence of chloride depassivates the steel, which initiates corrosion. The expansive corrosion product, when in sufficient amount, will cause the concrete to crack and eventually fall apart. External sulfate attack is based on the same principle. In that case, it is the penetration of sulfate ions in the concrete that is at the origin of the degradation. When the proper chemical conditions are met, the sulfates ions react with the solid phases of the material to form gypsum and ettringite. If the amount of these two products is important, severe cracking can occur, again leading to a degradation of the structure.

The reverse situation is also possible. Ions originally present in the concrete porous network as a result of cement hydration can be leached out of the material to the external environment. For example, a structure in contact with pure water will lose some of its hydroxyl ions, which causes a reduction of pH in the material. This drop of pH will lead to the dissolution of portlandite (calcium hydroxide) and the decalcification of C—S—H, the binding phase of the material. Consequently, the structure is bound to lose its mechanical resistance.

A good knowledge of ionic transport mechanisms in cement-based materials and the implementation of the related physical laws in a computer model would be necessary to evaluate properly the service-life of concrete structures. Such a model could be used to plan reparation schedules for structures, based on their estimated remaining service-life. It could also help to choose the proper concrete mixture for a given structure, given the environment to which it is exposed.

Despite this need, few significant developments related to the ionic transport in cement-based materials have been published in recent years. Most models used to predict the service-life of concrete structures are based on Fick's law, which simplifies the problem too much to yield reliable predictions.

Fick's law accounts for the transport of ions as a result of diffusion. The transport of particles by diffusion is the result of their thermal agitation which causes random collisions that eventually disperses the particles from high concentration regions to weak concentrations regions. When the particles are electrically charged like ions, their charge influences the transport by diffusion through the electrical coupling between the ions and the chemical activity of the solution. As a consequence, the movement of one ionic species is influenced by all the other species and the use of Fick's law is inappropriate.

The electrical coupling and the chemical activity effect emphasizes the multiionic aspect of ionic transport. Most of the time, the chloride ion is under scrutiny, as it is an important factor in the rebar corrosion phenomenon. However, few models consider the other ionic species involved in the transport process. They use Fick's law to model the transport of ions by diffusion. This approach is at the core of most ionic transport models in cement-based materials.

This is the case for example in the models published by Gospodinov et al. in "Diffusion of sulfate ions into cement stone regarding simultaneous chemical reactions and resulting effects" published in "Cement and Concrete Research", vol. 29, p.1591–1596 in 1999, by Hansen and Saouma, in "Numerical simulation of reinforced concrete deterioration—part 1: chloride diffusion", published in "ACI Materials Journal", vol. 96, no. 2, p. 173–180, 1999, by Martin-Pérez in "Service-life modeling of R. C. highway structures exposed to chlorides", in a Ph.D. thesis, University of Toronto, 1998, by Nagesh and Bhattacharjee in "Modeling of chloride diffusion in concrete and determination of diffusion coefficients", published in ACI Materials Journal, vol. 95, no. 2, p. 113–120, 1998, by Saetta et al. in "Analysis of chloride diffusion into partially saturated concrete", published in "ACI Materials" Journal, vol. 90, no. 5, p. 441–451, 1993, and Swaddiwudhipong et al. in, "Chloride ingress in partially and fully saturated concretes", published in "Concrete Science and Engineering", vol. 2, p. 17–31, 2000.

There are however an increasing number of papers where the electrical coupling is taken into account. This is the case for the work of Masi et al. in "Simulation of chloride penetration in cement-based materials", published in "Cement and Concrete Research", vol. 27, no. 10, p. 1591–1601, 1997 and Truc et al. in, "Numerical simulation of multi-species diffusion", published in, "Materials and Structures", vol. 33, p. 566–573, 2000. It should be emphasized that there are very few models accounting for the chemical activity effects. Li and Page in, "Modeling of electrochemical chloride extraction from concrete: influence of ionic activity coefficients", published in "Computational Materials Science", vol. 9, p. 303–308, 1998 include it in their model, as well as the electrical coupling. However, their model is limited to ionic transport in saturated cement-based systems exposed to an electrical current. It is not relevant to predict the service-life of concrete structures.

Ions can also move under the effect of fluid displacement in the porous network of the material. This phenomenon is called advection. This fluid displacement occurs as a result of capillary forces arising in unsaturated materials. A structure becomes unsaturated following the various wetting/drying cycles to which it is exposed during its service-life. In the models cited previously, only those of Martin-Pérez, Nagesh and Bhattacharjee, Saetta et al., and Swaddiwudhipong et al. consider capillary forces in unsaturated cement-based materials as a transport mechanism.

Both diffusion and advection drag the ions through the porous network of concrete. The ions may then undergo some chemical reactions with the hydrated cement paste. For example, the penetration of sulfate ($SO_4^{2-}$) ions in cement-based materials may lead to the formation of ettringite and gypsum, while the penetration of chloride is at the basis of the formation of chloroaluminates. Studies performed on simple cement systems clearly showed that these chemical reactions are multiionic. For instance, in addition to $SO_4^{2-}$, The formation of ettringite also involves $Ca^{2+}$, $OH^-$ and $Al(OH)_4^-$ ions. The last three ions are involved in the formation of chloroaluminates. Furthermore, the formation of ettringite, gypsum, and chloroaluminates is influenced by the presence of the alkali ions $Na^+$ and $K^+$.

Some studies have indicated that surface binding phenomena (also called physical adsorption) can have a significant influence on ionic transport mechanisms. This appears to be particularly the case for chloride penetration problems.

All of the previously cited models take into account interactions between ions in solution and the hydrated cement paste. They all use, without any exception, a simplified interaction model based on the concentration of only one ionic species. It is called the interaction isotherm, which consists in an experimental curve relating the amount of a given ion bound to the solid phase as a function of its concentration in solution. In most cases, the isotherm is determined for the chloride ions. This method is used in the model based on one ion as well as in the multiionic ones. Even if it allows to model the interactions involving chloride or sulfate, in most cases it does not allow to take into account other chemical reactions occurring simultaneously like the dissolution of portlandite or the decalcification of the C—S—H. The use of a simple chemical model thus limits the possibility of considering some reactions that are bound to have an important effect on the ionic transport in the material. Furthermore, it blends into one unique curve the chemical reactions, where products are formed or dissolved, with the surface interactions, where ions are adsorbed onto the surface.

Therefore, since it is essential to be able to determine the behavior of hydrated cement systems and concrete structures, there is a need for a method of calculating such a service-life accurately.

SUMMARY OF THE INVENTION

Accordingly, an object of the present invention is to provide a method and an apparatus for calculating a service-life for cement-based materials under chemical attacks.

Accordingly, another object of the present invention is to provide a calculation tool that allows to evaluate the variation over time of ionic profiles and solid phase contents in hydrated cement systems. It should take into account the following: the diffusion of multiple ionic species, the electrical coupling between ions, chemical activity effects, capillary suction, adsorption of ions and the dissolution/precipitation reactions.

Accordingly, another object of the present invention is to provide a calculation tool that allows to evaluate the diffusion coefficient of ions in a cement-based material.

According to an aspect of the present invention, there is provided a method for determining an ion concentration in solution for each of at least two ions capable of undergoing transport in a cement-based material under a chemical attack and a solid phase profile of at least one component of the cement-based material. The cement-based material has a solid skeleton in which liquid-filled and/or vapor-filled pores are found. The porosity of the cement-based material is provided. The method comprises the steps of determining a first concentration for each ion and an electrical potential profile using a transport algorithm, wherein the transport algorithm is a function of a diffusion of the ions, of an adsorption of the ions, of an electrical coupling between the ions and of a chemical activity effect and wherein the ionic solution of the material is not in equilibrium with the various solid phases of the hydrated cement paste of the cement-based material; calculating a corrected concentration for each ion and a corrected solid phase profile for the at least one of component using a chemical reactions algorithm, wherein at least one of dissolution and precipitation reactions is accounted for in order to maintain an equilibrium between the ionic solution and the various solid phases of the hydrated paste; calculating a changed transport properties profile to take into account an effect of the chemical reactions on the porosity of the material; and determining an ion concentration and a solid phase profile for at least one component using the changed transport properties profile and the corrected concentration and profile, wherein effects of the chemical reactions on the ionic transport are taken into account by correcting material transport properties and whereby the ion concentration for each ion and the solid phase profiles in the cement-based material can be used to evaluate a degradation of the cement-based material.

The transport algorithm can also be a function of the capillary suction if there is a relative humidity gradient. The water content is then further determined using said transport algorithm.

According to another aspect of the present invention, there is provided a method for determining a diffusion coefficient for each of at least two ions capable of undergoing transport in a cement-based material, said cement-based material having a solid skeleton and pores, said pores being at least one of liquid-filled and vapor-filled, a porosity of said cement-based material being provided, the method comprising the steps of: determining a concentration for each said at least two ions and an electrical potential profile using a transport algorithm, wherein the transport algorithm is a function of a diffusion of said at least two ions, of an electrical coupling between said at least two ions and a chemical activity of each said at least two ions; and determining a diffusion coefficient for each of at least two ions using said concentration and said electrical potential profile.

Preferably, the method further comprises providing input data, said input data comprising a set of tortuosity parameters and a measured electrical current for said material, determining a diffusion coefficient for each of said ions by 1. calculating a set of electrical currents each electrical current corresponding to one of said tortuosity parameter in said set of tortuosity parameters using said concentration, said electrical potential and each one of said tortuosity parameter in said set of tortuosity parameters; 2. choosing an electrical current from said set with a value closest to said measured electrical current; 3. determining a matching tortuosity parameter corresponding to said chosen electrical current; 4. determining said diffusion coefficient for each of said ions using said matching tortuosity.

According to another aspect of the present invention, there is provided an apparatus for determining an ion concentration in solution of each of at least two ions capable of undergoing transport in a cement-based material under a chemical attack and a solid phase profile of at least one component of the cement-based material. The apparatus comprises a first determiner for determining a first concentration for each ion and an electrical potential profile using a transport algorithm; a first calculator for calculating a corrected concentration for each ion and a corrected solid phase profile for the at least one of component using a chemical reactions algorithm; a second calculator for calculating a changed transport properties profile to take into account an effect of the chemical reactions on the porosity of the material; and a second determiner for determining an ion concentration and a solid phase profile for at least one component using the changed transport properties profile and the corrected concentration and profile.

According to still another aspect of the present invention, there is provided an apparatus for determining a diffusion coefficient for each of at least two ions capable of undergoing transport in a cement-based material. The apparatus comprises a first determiner for determining a concentration for each ion and an electrical potential profile using a transport algorithm, and a second determiner for determining a diffusion coefficient for each ion using the concentration and the electrical potential profile.

Preferably, the apparatus further comprises an input data provider for providing input data, the input data comprising a set of tortuosity parameters and a measured electrical current for the material and a third determiner for determining a diffusion coefficient for each ion by 1. calculating a set of electrical currents each electrical current corresponding to one of the tortuosity parameter in the set of tortuosity parameters using the concentration, the electrical potential and each one of the tortuosity parameter in the set of tortuosity parameters; 2. choosing an electrical current from the set with a value closest to the measured electrical current; 3. determining a matching tortuosity parameter corresponding to the chosen electrical current; 4. determining the diffusion coefficient for each of the ions using the matching tortuosity.

BRIEF DESCRIPTION OF THE DRAWINGS

These and other features, aspects and advantages of the present invention will become better understood with regard to the following description and accompanying drawings wherein:

FIG. 1 is a flow chart of an overview of a preferred algorithm according to the invention;

DETAILED DESCRIPTION OF THE MORE PREFERRED EMBODIMENT

Figure 2A:
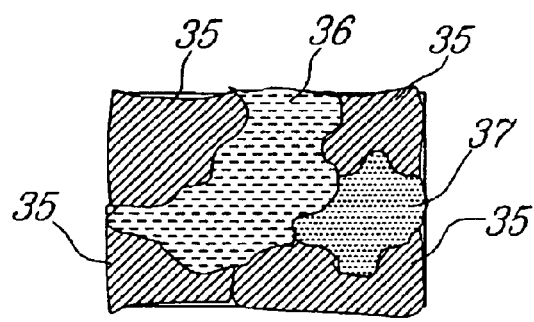
FIG. 2a is an illustration of a representative elementary volume (REV)

An algorithm useful to the understanding of this invention was first described by Grove and Wood in "Prediction and field verification of subsurface-water quality during artificial recharge", Lubbock, Tex., Groundwater, vol. 17, no. 3, p. 250–257, 1979. It separates the transport of ions from the chemical reactions. During a single time step, the equations for ionic transport are first solved, without considering any chemical reactions. At the end of this step, the concentration profiles are known. However, the concentration of various points in the material may not be in equilibrium with the phases forming the solid skeleton of the material. Then starts the chemical step. The concentration profiles are corrected according to dissolution/precipitation reactions in order to maintain the equilibrium between the solution and the different solid phases. After the chemical step, the concentration profiles in solution as well as the solid concentration profiles are known.

The most preferred embodiment is summarized in FIG. 1. The calculation starts from input data giving the initial state of the material, its transport properties and some numerical parameters: porosity, temperature, ionic pore solution concentrations, amount of each solid phase, diffusion coefficient for each ionic species, water diffusivity, initial water content, the number of time steps and their length, and the finite element mesh. Boundary conditions are also provided to start the calculation. The calculation for the first time step begins. The invention performs a transport step, in which the ionic profiles are modified. These ionic profiles and the amount of the various solid phases are then corrected in the chemical step following dissolution and precipitation reactions in order to maintain the equilibrium between the pore solution and the hydrated paste. The invention then goes back to the transport step and begins the second time step, and so on. At the end of the calculation, the output of the invention is concentration and solid phase content profiles in the materials at various time steps.

It will be readily understood by one skilled in the art that in order to solve the transport equations, any numerical method could have been used. The preferred numerical method for solving the transport equations is the finite elements method. However, the finite differences and the finite volumes methods could be used without departing from the present invention.

The transport step 26 is summarized as follows. In the transport step, the movement of ions is modeled by the extended Nernst-Planck equation with an advection term. This equation accounts for the electrical coupling between the ions as well as the chemical activity effects. The latter is calculated on the basis of a modified Davies equation that describes well the behavior of highly concentrated ionic solutions, such as those commonly found in cement-based materials. The advection term takes into account the movement of fluid arising when the material is exposed to gradient of relative humidity. A mass conservation equation is considered for each ionic species. This mass conservation equation includes a term to account for ionic adsorption. To estimate the electrical potential in the material caused by the electrical coupling between the ions, Poisson's equation is used. The last equation considered is Richards', which is used to calculate the water content distribution in the porous network. The system of equations is solved using the finite element method.

The chemical reaction model of dissolution and precipitation 27 is summarized as follows. After a transport step, the solution in the pores is not in thermodynamic equilibrium with the various solid phases of the hydrated cement paste. To restore to the equilibrium state, the invention uses a chemical equilibrium code. It adjusts both the pore solution and the solid phase content. The equilibrium is calculated on the basis of the chemical equilibrium relationships of dissolution/precipitation reactions. It is assumed that the velocity of the ions is slow compared to the kinetics of the chemical reactions. This is called the local equilibrium hypothesis. Under this hypothesis, the chemical equilibrium relationships are valid.

During the course of the ionic transport process, the dissolution of some phases will locally increase the porosity in the material, thus allowing the ions to move more rapidly in a structure. On the contrary, the precipitation of some solid will reduce the section of the pores and slow the ionic movement. The effects of the chemical reaction on the ionic transport are taken into account by correcting the material transport properties as a function of the porosity in step 28. This particular aspect of the invention is not present in any of the prior art models. A check is made at step 29 to ensure that all time steps have occurred. The output 30 comprises ionic concentration profiles, solid phase profiles, water content profile and electrical potential profile.

A few assumptions had to be made prior to creating the model of the present invention. The model was designed under the hypothesis of a constant temperature. The solid phase is assumed non-deformable. External mechanical forces are thus not considered neither are cracks formed in the material. The calculations are performed assuming a constant hydration state. Finally, the hydrated products forming the solid phase are assumed to be uniformly distributed throughout the latter. The model is presented for the 1D case. Although these assumptions are used in the model of the preferred embodiment, it will be understood that modifications to the model to change these assumptions do not depart from the present invention.

Transport Model

To model the transport of ions, which occur in the liquid (aqueous) phase, the equations are first written at the microscopic scale. They are then integrated over a Representative Elementary Volume (REV), as shown in FIG. 2a, using the homogenization (averaging) technique, to yield the equations at the macroscopic scale. The REV comprises a solid skeleton 35 and pores containing solution 36 and/or a gaseous phase 37. An example of an arrangement of such pores is shown in FIG. 2a. Details on the averaging technique can be found in Bear et al., "Introduction to Modeling of Transport Phenomena in Porous Media", Kluwer Academic Publishers (Netherlands), 1991 and in Samson et al., "Describing ion diffusion mechanisms in cement-based materials using the homogenization technique", Cement and Concrete Research, vol. 29, no. 8, p. 1341–1345, 1999.

Figure 2B:
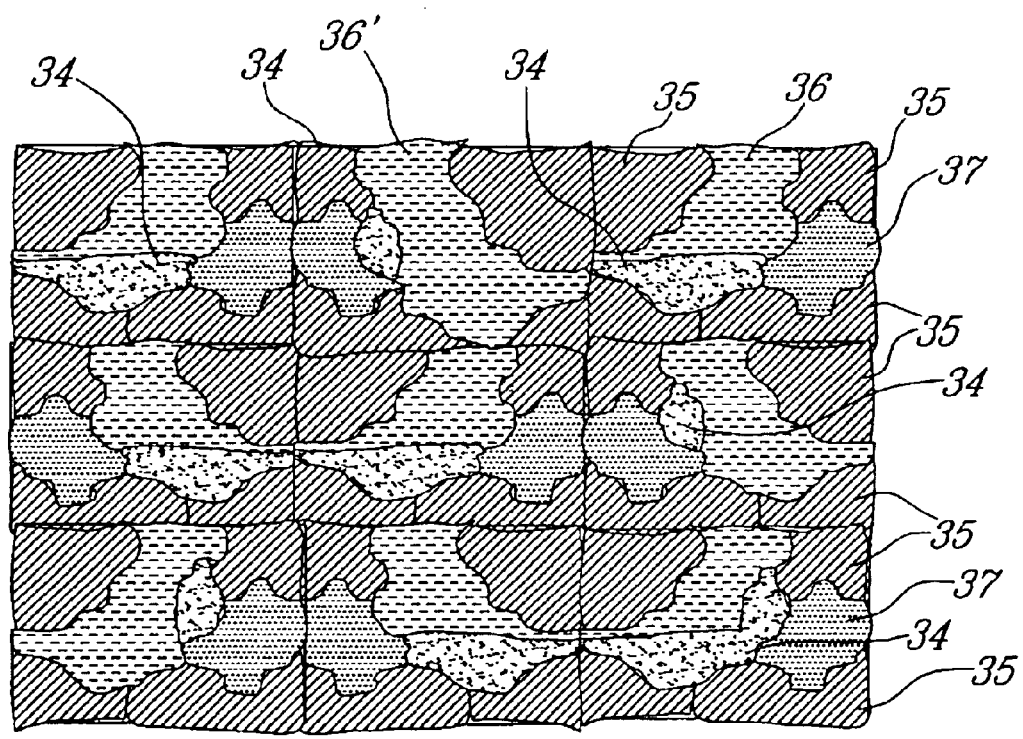
FIG. 2b is an illustration of a plurality of REVs in which the pores are being filled with precipitates and solutes.

The transport of ions may create precipitates 34 in the solution-filled pores 36 as is shown in FIG. 2b. FIG. 2b shows a plurality of REVs making up a portion of the cement-based material. The precipitates 34, as the precipitation occurs, fill up the solution-filled pores 36 and eliminate a portion of the solution-filled pores 36. This creates a change in the porosity of the material and affects its transport properties. The solutes increase the porosity of the material by mixing in with the solution in the solution-filled pores 36 and increasing their size, see for example pore 36' which has been filled up by solutes.

The macroscopic equation for the transport of ionic species i is based on the extended Nernst-Planck equation with an advection term. Once integrated over the REV, it gives:

$$\frac{\partial(\theta_s c_i^s)}{\partial t} + \frac{\partial(\theta c_i)}{\partial t} - \tag{1}$$

$$\frac{\partial}{\partial t}\left(\underbrace{\theta D_i \frac{\partial c_i}{\partial x}}_{\text{diffusion}} + \underbrace{\theta \frac{D_i z_i F}{RT} c_i \frac{\partial \psi}{\partial x}}_{\text{electrical coupling}} + \underbrace{\theta D_i c_i \frac{\partial \ln \gamma_i}{\partial x}}_{\text{chemical activity}} - \underbrace{c_i V_x}_{\text{advection}}\right) = 0$$

where $c_i$ is the concentration of the species i in solution, $c_i^s$ is the concentration in solid phase, $\theta_s$ is the volumetric solid content of the material, $\theta$ is the volumetric water content in the porous network, $D_i$ is the diffusion coefficient, $z_i$ is the valence number of the species, F is the Faraday constant, R is the ideal gas constant, T is the temperature of the material, $\psi$ is the electrical potential, $\gamma_i$ is the chemical activity coefficient and $V_x$ is the average velocity of the fluid in the pore system under the action of capillary suction.

This equation is very different from classical diffusion model where only the term bearing the <<diffusion>> label in equation (1) usually appears. This term models the movement of the ions as a result of their thermal agitation. It is best known as Fick's law.

But ions in solution bear electrical charges. As ions have different drifting velocities, the fastest ions tend to separate from the slower ones. However, since charges of opposite signs mutually attract each other, the faster ions are slowed down and the slowest ones are accelerated, in order to bring the system near the electroneutral state. This creates an electrical potential $\psi$ in the material. This term is labeled <<electrical coupling>> in equation (1). To take this potential into account, Poisson's equation is added to the model. It is given here after being averaged over the REV:

$$\frac{d}{dx}\left(\tau\theta\frac{d\psi}{dx}\right) + \frac{F}{\varepsilon}\theta\left(\sum_{i=1}^{N} z_i c_i\right) = 0 \quad (2)$$

where $\tau$ is the tortuosity of the porous network, $\varepsilon$ is the dielectric permittivity of the solution and N is the total number of ionic species. The validity of this equation is based on the assumption that the electromagnetic signal travels much more rapidly than ions in solutions. This allows considering an equation from electrostatics in a transient problem.

The next term in equation (1) that differs from a classical diffusion model is related to the chemical activity of the ionic species. To calculate the chemical activity coefficients $\gamma_i$s, several models are available. However, well-known models such as Debye-Hückel or Davies are unable to cope with the specific case of cement-based materials, which bears a highly charged pore solution. A modification of Davies' relationship was found to yield good results:

$$\ln\gamma_i = -\frac{Az_i^2\sqrt{I}}{1+a_iB\sqrt{I}} + \frac{(0.2 - 4.17\times 10^{-5}I)Az_i^2 I}{\sqrt{1000}} \quad (3)$$

where I is the ionic strength of the solution:

$$I = \frac{1}{2}\sum_{i=1}^{N} z_i^2 c_i \quad (4)$$

In equation (4), A and B are temperature dependent parameters, given by:

$$A = \frac{\sqrt{2}\,F^2 e_o}{8\pi(\varepsilon RT)^{3/2}} \quad (5)$$

$$B = \sqrt{\frac{2F^2}{\varepsilon RT}} \quad (6)$$

where $e_o$ is the electrical charge of one electron, $\varepsilon=\varepsilon_r\varepsilon_o$ is the permittivity of the medium, given by the dielectric constant times the permittivity of the vacuum. Finally, the parameter $a_i$ in equation (3) depends on the ionic species. Its value is $3\times10^{-10}$ for OH$^-$, $3\times10^{-10}$ for Na$^+$, $3.3\times10^{-10}$ for K$^+$, $1\times10^{-10}$ for SO$_4^{2-}$, $2\times10^{-10}$ for Cl$^-$ and $1\times10^{-13}$ for Ca$^{2+}$.

The movement of water in the pore network under the effect of capillary suction is modeled with Richard's equation. This equation is developed under the following hypothesis: isothermal conditions, isotropic material, non-deformable solid matrix, negligible gravitational effect, water movement slow enough to have equilibrium between the liquid and the gaseous phase, and a uniform pressure in both phases. The equation is given by:

$$\frac{\partial\theta}{\partial t} - \frac{\partial}{\partial x}\left(D_\theta\frac{\partial\theta}{\partial x}\right) = 0 \quad (7)$$

where $D_\theta$ is the moisture diffusivity coefficient. It is the sum of the diffusivity coefficient of vapor and water. An expression is also needed for the average speed of the liquid phase, which appears in equation (1). It is given by:

$$V_x = -D_L\frac{\partial\theta}{\partial x} \quad (8)$$

where $D_L$ is the water diffusivity coefficient. Equation (8) allows to transform equation (1) as:

$$\frac{\partial(\theta_s c_i^s)}{\partial t} + \frac{\partial(\theta c_i)}{\partial t} - \frac{\partial}{\partial t}\left(\theta D_i\frac{\partial c_i}{\partial x} + \theta\frac{D_i z_i F}{RT}c_i\frac{\partial\psi}{\partial x} + \theta D_i c_i\frac{\partial\ln\gamma_i}{\partial x} + D_L c_i\frac{\partial\theta}{\partial x}\right) = 0 \quad (9)$$

The first term on the left-hand side of equation (9), involving $c_i^s$, describes the exchange between the solid and the aqueous phase, i.e. the ionic interactions. As shown in Rubin J., "Transport of reacting solutes in porous media: relation between mathematical nature of problem formulation and chemical nature of reactions", Water Resources Research, vol. 19, no. 5, p. 1231–1252, 1983, this term can be used to model both the adsorption and the dissolution/precipitation reactions. For the model presented here, it will only be used to model adsorption. Adsorption is modeled through an adsorption isotherm that relates $c_i^s$ to the concentration of that ionic species in solution $c_i$: $c_i^s=f(c_i)$. Depending on the material and on the ionic species in solution, the adsorption isotherm can have different forms. Here are some typical adsorption isotherm models:

$c_i^s = Kc_i$ linear isotherm (10)

$c_i^s = Kc_i^m$ Freundlich isotherm (11)

$$c_i^s = \frac{Kc_i}{1+Gc_i} \quad \text{linear isotherm} \quad (12)$$

where K, G and m are constant to be determined experimentally. Once the isotherm is known, it is substituted in equation (9) knowing that:

$$\frac{\partial c_i^s}{\partial t} = \frac{\partial c_i^s}{\partial c_i}\frac{\partial c_i}{\partial t} \quad (13)$$

which gives:

$$\left[\theta_s\left(\frac{\partial c_i^s}{\partial c_i}\right) + \theta\right]\frac{\partial c_i}{\partial t} + c_i\frac{\partial\theta}{\partial t} - \frac{\partial}{\partial t}\left(\theta D_i\frac{\partial c_i}{\partial x} + \theta\frac{D_i z_i F}{RT}c_i\frac{\partial\psi}{\partial x} + \theta D_i c_i\frac{\partial\ln\gamma_i}{\partial x} + D_L c_i\frac{\partial\theta}{\partial x}\right) = 0 \quad (14)$$

To get equation (14), it is assumed that the time variation of $\theta_s$ are small.

The transport part of the model is complete. The unknowns are $\psi$, $\theta$ and N times $c_i$, i.e. a concentration for each ionic species taken into account. There is accordingly N equations (14), one for each concentration, equation (2) to solve the electrical potential and equation (7) for the water content. The other parameters are either physical constants, like F, R, $z_i$, $e_o$, $\varepsilon$, or parameters that have to be determined experimentally: T, $\theta_s$, $D_i$, $\tau$, $D_\theta$, $D_L$, $\partial c_i^s/\partial c_i$.

To solve this system of nonlinear equations, the finite element method is used. Details are given in the following paragraphs. To ease the writing, the numerical model will be shown for a two ion case in 1D. But the model can easily be extended to take into account more species. The numerical examples discussed below involve six ions.

The finite element method requires one to write the equations under their weighted residual form. The weighted residual form, upon integration by parts, is given as:

$$W = \int_L \langle \delta\Psi \rangle \begin{bmatrix} \theta + \theta_s \frac{\partial c_1^s}{\partial c_1} & 0 & c_1 & 0 \\ 0 & \theta + \theta_s \frac{\partial c_2^s}{\partial c_2} & c_2 & 0 \\ 0 & 0 & 1 & 0 \\ 0 & 0 & 0 & 0 \end{bmatrix} \begin{Bmatrix} \dot{c}_1 \\ \dot{c}_2 \\ \dot{\theta} \\ \dot{\psi} \end{Bmatrix} dx + \quad (15)$$

$$\int_L \left\langle \frac{\partial \delta\Psi}{\partial x} \right\rangle \begin{bmatrix} \theta D_1 & 0 & D_L c_1 & \frac{D_1 z_1 F}{RT}\theta c_1 \\ 0 & \theta D_2 & D_L c_2 & \frac{D_2 z_2 F}{RT}\theta c_2 \\ 0 & 0 & D_\theta & 0 \\ 0 & 0 & 0 & \theta\tau \end{bmatrix} \begin{Bmatrix} c_{1,x} \\ c_{2,x} \\ \theta_x \\ \psi_{,x} \end{Bmatrix} dx + \quad (15)$$

$$\int_L \left\langle \frac{\partial \delta\Psi}{\partial x} \right\rangle \begin{bmatrix} \theta D_1 \frac{\partial(\ln\gamma_1)}{\partial x} & 0 & 0 & 0 \\ 0 & \theta D_2 \frac{\partial(\ln\gamma_2)}{\partial x} & 0 & 0 \\ 0 & 0 & 0 & 0 \\ 0 & 0 & 0 & 0 \end{bmatrix} \begin{Bmatrix} c_1 \\ c_2 \\ \theta \\ \psi \end{Bmatrix} dx +$$

$$\int_L \langle \delta\Psi \rangle \begin{bmatrix} 0 & 0 & 0 & 0 \\ 0 & 0 & 0 & 0 \\ 0 & 0 & 0 & 0 \\ -\frac{F}{\varepsilon}z_1\theta & -\frac{F}{\varepsilon}z_2\theta & 0 & 0 \end{bmatrix} \begin{Bmatrix} c_1 \\ c_2 \\ \theta \\ \psi \end{Bmatrix} dx = 0$$

where $\langle \delta\Psi \rangle$ is the vector of the weighting function, defined as:

$$\langle \delta\Psi \rangle = \langle \delta c_1 \; \delta c_1 \; \delta\theta\delta\psi \rangle \quad (16)$$

The boundary terms are omitted since only Dirichlet and natural boundary conditions will be considered in the simulations.

The weak form is discretized using the well-known Galerkin method with a standard linear two-node element (see Reddy J. N., Gartling D. K., "The finite element method in heat transfer and fluid dynamics", CRC Press (USA), 1994). for a complete text on the method). The approximation of the solution on each element is written as:

$$\begin{Bmatrix} c_1 \\ c_2 \\ \theta \\ \psi \end{Bmatrix} = [N]\{U_n\} \quad (17)$$

$$[N] = \begin{bmatrix} N_1 & 0 & 0 & 0 & N_2 & 0 & 0 & 0 \\ 0 & N_1 & 0 & 0 & 0 & N_2 & 0 & 0 \\ 0 & 0 & N_1 & 0 & 0 & 0 & N_2 & 0 \\ 0 & 0 & 0 & N_1 & 0 & 0 & 0 & N_2 \end{bmatrix} \quad (18)$$

$$\langle U_n \rangle = \langle c_{11} c_{21} \theta_1 \psi_1 c_{12} c_{22} \theta_2 \psi_2 \rangle \quad (19)$$

where $N_1$ and $N_2$ are the shape functions. The subscripts i and j for the concentrations in the vector $\langle U_n \rangle$ (equation 19) designate the species i at the node j of one element. The elementary matrices are thus expressed as:

$$[K^e] = \int_{l^e} ([B]^T[D_1][B] + [B]^T[D_2][N] + [N]^T[D_3][N])\,dx \quad (20)$$

$$[M^e] = \int_{l^e} ([N]^T[C][N])\,dx \quad (21)$$

with $$[B] = \begin{bmatrix} N_{1,x} & 0 & 0 & 0 & N_{2,x} & 0 & 0 & 0 \\ 0 & N_{1,x} & 0 & 0 & 0 & N_{2,x} & 0 & 0 \\ 0 & 0 & N_{1,x} & 0 & 0 & 0 & N_{2,x} & 0 \\ 0 & 0 & 0 & N_{1,x} & 0 & 0 & 0 & N_{2,x} \end{bmatrix} \quad (22)$$

$$[D_1] = \begin{bmatrix} \theta D_1 & 0 & D_L c_1 & \frac{D_1 z_1 F}{RT}\theta c_1 \\ 0 & \theta D_2 & D_L c_2 & \frac{D_2 z_2 F}{RT}\theta c_2 \\ 0 & 0 & D_\theta & 0 \\ 0 & 0 & 0 & \theta\tau \end{bmatrix} \quad (23)$$

$$[D_2] = \begin{bmatrix} \theta D_1 \frac{\partial(\ln\gamma_1)}{\partial x} & 0 & 0 & 0 \\ 0 & \theta D_2 \frac{\partial(\ln\gamma_2)}{\partial x} & 0 & 0 \\ 0 & 0 & 0 & 0 \\ 0 & 0 & 0 & 0 \end{bmatrix} \quad (24)$$

$$[D_3] = \begin{bmatrix} 0 & 0 & 0 & 0 \\ 0 & 0 & 0 & 0 \\ 0 & 0 & 0 & 0 \\ -\frac{F}{\varepsilon}z_1\theta & -\frac{F}{\varepsilon}z_2\theta & 0 & 0 \end{bmatrix} \quad (25)$$

$$[C] = \begin{bmatrix} \theta + \theta_s \frac{\partial c_1^s}{\partial c_1} & 0 & c_1 & 0 \\ 0 & \theta + \theta_s \frac{\partial c_2^s}{\partial c_2} & c_2 & 0 \\ 0 & 0 & 1 & 0 \\ 0 & 0 & 0 & 0 \end{bmatrix} \quad (26)$$

The assembly of elementary matrices $[K^e]$ and $[M^e]$ leads to the following system of equations:

$$[M]\{\dot{U}\} + [K]\{U\} = 0 \quad (27)$$

The time discretization is performed using the implicit Euler scheme:

$$[M_t]\left\{\frac{U_t - U_{t-\Delta t}}{\Delta t}\right\} + [K_t]\{U_t\} = 0 \quad (28)$$

where $\Delta t$ is the time step. The subscript t stands for the actual time step and $t-\Delta t$ the previous one. Defining the matrices $$[\overline{K}] = [M_t] + \Delta t[K_t] \quad (29)$$

$$[\overline{F}] = [M_t]\{U_{t-\Delta t}\} \quad (30)$$

the system of equations can be written as:

$$[\overline{K}]\{U_t\} = \{\overline{F}\} \quad (31)$$

where $\{U_t\}$ is the vector of unknowns. This nonlinear system of equations is solved at each time step with the modified iterative Newton-Raphson method. Numerical simulations have shown that the convergence rate with a tangent matrix calculated without the nonlinear terms arising from the coupling between the various variables in the model is almost as fast as the one with a complete tangent matrix. However, the calculation time is reduced since less terms need to be calculated. Furthermore, its wider radius of convergence makes this algorithm even more interesting. The elementary tangent matrix is thus given as:

$$[K_T^e] = [M^e] + \Delta t [K^e] \quad (32)$$

Following Newton's method, the solution $\{U_t\}$ is obtained by successive iterations k according to:

$$[K_T^{k-1}]\{\Delta u^k\} = -([\overline{K}^{k-1}]\{U_t^{k-1}\} - \{\overline{F}^{k-1}\}) \quad (33)$$

This system of equations is solved for $\{\Delta u^k\}$ with Gauss elimination method and the solution is updated at each iteration:

$$\{U_t^k\} = \{U_t^{k-1}\} + \{\Delta u^k\} \quad (34)$$

Several iterations are performed over equations (33) and (34) until the increment $\{\Delta u^k\}$ becomes sufficiently small. When convergence is reached, the solution $\{U_t\}$ at this time step is known, i.e. the variables $c_i$, $\psi$ and $\theta$ are known.

The elementary matrices in equations (20) and (21) are evaluated through Gauss numerical integration method. Accordingly, the variables appearing in the matrices $[D_1]$, $[D_2]$, $[D_3]$, and $[C]$ are calculated at the integration points. To calculate the terms $\partial(\ln\gamma_i)/\partial x$ in (24), the ionic strength (equation 4) is calculated at each node. Then the $\ln\gamma_i$s are calculated for each species and at each node with equation (3). From there, the value of $\partial(\ln\gamma_i)/\partial x$ can be evaluated at every integration point.

Chemical Reaction Model

The chemical reactions considered in the invention are of the dissolution/precipitation type. The solids considered are listed in table 1. However, the algorithm presented is very general and could be applied to other solid phases as well.

which gives the correction needed to reach equilibrium. This procedure must be applied to all solid phases. At the end of this calculation step, all solid phases are in equilibrium with all ions in solution. The algorithm is detailed here:

1. Calculate the activity product $\gamma_{Ca}\gamma_{OH}^2 C_{Ca} C_{OH}^2$.
2. If the activity product is under the equilibrium constant and there is still some portlandite left, then there will be dissolution. If the activity product is over the equilibrium constant, there will be precipitation. In both cases, equation (36) is solved according to these calculation steps:

a) Solve equation (36) assuming constant chemical activity coefficients with the Newton-Raphson method. This gives the following recursive formula:

$$\Delta c_{Ca}^k = \quad (37)$$

$$\Delta c_{Ca}^{k-1} - \frac{\gamma_{Ca}\gamma_{OH}^2(c_{Ca}^o + \Delta c_{Ca}^{k-1})(c_{OH}^o + 2\Delta c_{Ca}^{k-1})^2 - K_{sp}}{\gamma_{Ca}\gamma_{OH}^2[4(c_{Ca}^o + \Delta c_{Ca}^{k-1})(c_{OH}^o + 2\Delta c_{Ca}^{k-1}) + (c_{OH}^o + 2\Delta c_{Ca}^{k-1})^2]}$$

As stated earlier, the subscript o indicates the concentration value before the equilibrium calculation.

b) Calculate new chemical activity coefficients with the concentrations $(c_{Ca}^o + \Delta C_{Ca}^k)$ and $(c_{OH}^o + 2\Delta c_{Ca}^k)$.

c) Go back to step (a) with the new chemical activity coefficients.

d) Repeat steps (a) to (c) until the activity product $\gamma_{Ca}\gamma_{OH}^2 C_{Ca} C_{OH}^2$ is near the equilibrium value $K_{sp}$, according to a given threshold value. When equilibrium is reached for that particular phase, the concentrations are corrected with the last value of $\Delta C_{Ca}^k$ found.

3. Repeat steps (1) and (2) for the other solid phases (see table 1).

4. After each solid phase has been considered, verify if the corrected solution is in equilibrium with all solid phases. If

TABLE 1

Solid phases in hydrated cement paste

| Name | Chemical formula | Expression for equilibrium | Value[#] |
|---|---|---|---|
| Portlandite | $Ca(OH)_2$ | $K_{sp} = \{Ca\}\{OH\}^2$ | 5.2 |
| C—S—H | $1.65CaO.SiO_2.(2.45)H_2O$[$] | $K_{sp} = \{Ca\}\{OH\}^2$[¶] | 5.6[¶] |
| Ettringite | $3CaO.Al_2O_3.3CaSO_4.32H_2O$ | $K_{sp} = \{Ca\}^6\{OH\}^4\{SO_4\}^3\{Al(OH)_4\}^2$ | 44.4 |
| Friedel's salt | $3CaO.Al_2O_3.CaCl_2.10H_2O$ | $K_{sp} = \{Ca\}^4\{OH\}^4\{Cl\}^2\{Al(OH)_4\}^2$ | 29.1 |
| Hydrogarnet | $3CaO.Al_2O_3.6H_2O$ | $K_{sp} = \{Ca\}^3\{OH\}^4\{Al(OH)_4\}^2$ | 23.2 |
| Gypsum | $CaSO_4.2H_2O$ | $K_{sp} = \{Ca\}\{SO_4\}$ | 4.6 |
| Mirabilite | $Na_2SO_4.10H_2O$ | $K_{sp} = \{Na\}^2\{SO_4\}$ | 1.2 |

Where { . . . } indicates chemical activity, [$]indicates that the C—S—H is considered having a C/S ratio of 1.65, [¶]indicates that the C—S—H decalcification is modeled as the portlandite dissolution with a lower solubility and [#]indicates the value of the equilibrium constant (-log $K_{sp}$).

The equilibrium between the solid phases and the solution is checked at each node of the finite element mesh. It is calculated as follow. Consider for example the case of portlandite (see Table 1). Its equilibrium constant is expressed as:

$$K_{sp} = \{Ca\}\{OH\}^2 \quad (35)$$

where the curly brackets { . . . } indicate chemical activity. Knowing that the activity is equal to $\gamma_i c_i$ and that in portlandite, for each $Ca^{2+}$ there is two $OH^-$, equation (35) is transformed as:

$$K_{sp} = \gamma_{Ca}\gamma_{OH}^2(c_{Ca}^o + \Delta c_{Ca})(c_{OH}^o + 2\Delta c_{Ca})^2 \quad (36)$$

where the subscript o indicates the concentration value before equilibrium. This equation must be solved for $\Delta c_{Ca}$, this is not the case, repeat steps (1) to (3) until the equilibrium state is reached (again within a given threshold value).

After this calculation, the concentrations in solution have been adjusted in order to respect the equilibrium expressions given in Table 1, indicating that dissolution and/or precipitation reactions occurred. The solid phases must be corrected accordingly at each node of the finite element mesh. To do so, the variations in concentration for each ions must be associated with the proper solid. For example, the total variation of calcium, before and after equilibrium was made, can come from the dissolution of portlandite, the dissolution of hydrogarnet and the precipitation of ettringite, since all these solids contain calcium. Assume that at a given node, there are variations of concentration in $Ca^{2+}$, $SO_4^{2-}$ and $Al(OH)_4^-$, and that portlandite and hydrogarnet are present at this location. One can thus write:

$$\Delta_{SO4}{}^{Tot}=\Delta_{SO4}{}^{Ettringite} \quad (38)$$

$$\Delta_{Al}{}^{Tot}=\Delta_{Al}{}^{Ettringite}+\Delta_{Al}{}^{Hydrogarnet} \quad (39)$$

$$\Delta_{Ca}{}^{Tot}=\Delta_{Ca}{}^{Ettringite}+\Delta_{Ca}{}^{Hydrogarnet}+\Delta_{Ca}{}^{Portlandite} \quad (40)$$

where the $\Delta^{Tot}$ quantities correspond to the variation in concentration after and before the equilibrium was made. The other $\Delta$s correspond the fraction of the variations associated with each solid involved. Equations (38) to (40) are solved, knowing that $\Delta_{Al}{}^{Ettringite}=\frac{2}{3}\Delta_{SO4}{}^{Ettringite}$ since in ettringite, for 2 moles of alumina, there is 3 moles of sulfate, and that $\Delta_{Ca}{}^{Ettringite}=2\Delta_{SO4}{}^{Ettringite}$ and $\Delta_{Ca}{}^{Hydrogarnet}=\frac{3}{2}\Delta_{Al}{}^{Hydrogarnet}$, for similar reasons. Once $\Delta_{SO4}{}^{Ettringite}$, $\Delta_{Al}{}^{Hydrogarnet}$, and $\Delta_{Ca}{}^{Portlandite}$ are know, they are translated into the proper amount of solid.

The study of cement systems exposed to sulfate ions revealed that hydrogarnet and gypsum are two phases that do not coexist. Gypsum can only form after all hydrogarnet has been dissolved. These observations are taken into account in step 3, to avoid performing equilibrium on both hydrogarnet and gypsum.

The C—S—H is treated in a particular way. When in contact with a low pH solution, the C—S—H phase loses its calcium, a phenomenon called decalcification. It leaves in place a silica gel. To model this chemical reaction, the C—S—H will be considered as portlandite, but with a lower solubility constant (see Table 1). Its decalcification will thus release $Ca^{2+}$ and $OH^-$ ions.

The chemical reactions, besides binding or releasing ions while solid phases are precipitated or dissolved, will have an effect on the transport properties by affecting the porosity of the material. If, for example, gypsum is formed at some place, it will reduce the porosity at that location, thus reducing the section across which ions are able to diffuse. This will reflect on their diffusion coefficient, according to an equation presented by Garboczi and Bentz in "Computer simulation of the diffusivity of cement-based materials", Journal of Material Science, vol. 27, p. 2083–2092, 1992:

$$\frac{D_i}{D_i^\mu} = 0.001 + 0.07\phi_{cap}^2 + 1.8 \times H(\phi_{cap} - 0.18)(\phi_{cap} - 0.18)^2 \quad (41)$$

where $\phi_{cap}$ is the capillary porosity of the paste, $D_i^\mu$ is the diffusion coefficient of ionic species i in free water (as opposed to a porous material) and H is the Heaviside function such that $H(x)=1$ for $x>0$ and $H(x)=0$ for $x \leq 0$. The initial capillary porosity can be calculated with the following relationship:

$$\phi_{cap}^{init} = \frac{(w/c) - 0.36\alpha}{(w/c) + 0.32} \quad (42)$$

where w/c is the water/cement ratio of the cement paste and $\alpha$ is the degree of hydration of the paste ($0 \leq \alpha \leq 1$). Upon chemical modification to the paste, the capillary porosity is calculated as:

$$\phi_{cap} = \phi_{cap}^{init} + \sum_{s=1}^{M} (V_s^{init} - V_s) \quad (43)$$

where $V_s$ is the volume of a given solid phase, per unit volume of cement paste, and M is the total number of solid phases. Based on this model, the correction factor G that multiplies the diffusion coefficients $D_i$ of each ionic species is calculated as follow:

$$G = \frac{\left.\frac{D_i}{D_i^\mu}\right|_{Modified\ paste}}{\left.\frac{D_i}{D_i^\mu}\right|_{Initial\ paste}} \quad (44)$$

Again, the case of C—S—H is treated separately. The silica gel remaining after the decalcification process has no structural strength. When at a given location the decalcification is completed, the damage factor G is set to ten.

Figure 18:
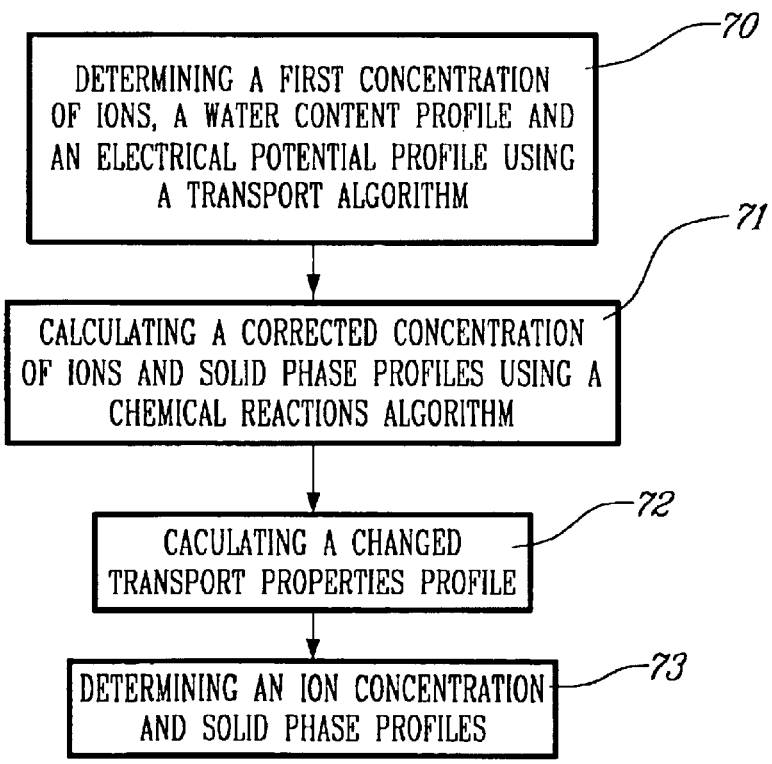
FIG. 18 is a flow chart of the main steps of the most preferred embodiment of the present invention.

FIG. 18 is a flow chart of the main steps of the most preferred embodiment of the present invention. The preferred embodiment is a method for determining an ion concentration for each of at least two ions capable of undergoing transport in a cement-based material under a chemical attack and a solid phase profile for at east one component of the cement-based material. The method comprises the steps of determining 70 a first concentration for each ion and an electrical potential profile using a transport algorithm. The water content profile can also be determined by the transport algorithm. The next step is calculating 71 a corrected concentration for each ion and solid phase profiles using a chemical reactions algorithm, wherein dissolution and/or precipitation reactions are accounted for. The next step is calculating 72 a changed transport properties profile to take into account an effect of the chemical reaction equilibrium on the porosity of the material. Finally, the last step is determining 73 an ion concentration and solid phase profiles using the changed transport properties profile and the corrected concentration and profile.

DESCRIPTION OF ANOTHER PREFERRED EMBODIMENT

The main parameter that characterizes ionic transport in porous materials is the diffusion coefficient $D_i$. This parameter can be determined with diffusion tests, but they are time consuming, their duration extending over several months. Since two decades, the migration test is more commonly used. The experimental setup is similar to the diffusion test (see FIG. 3). It consists in a cement-based material disk 40 located between two cells containing different solutions. Both cells contain a solution of NaOH in order to avoid the degradation of the material. The upstream cell 38 also contains one of these salt: NaCl, KCl, $Na_2SO_4$. Prior to the test, the disk is immersed in a NaOH solution under vacuum for at least 24 hours to saturate the pores. Watertight joints prevent any leakage between the sample and the cells. As a result of diffusion, the ions of this salt will move through the sample to the downstream cell 41. The measurement of the ionic flux through the sample is used to evaluate the diffusion coefficients of the ionic species. In the case of the migration test, the ions are accelerated with an electrical field 43, which reduces the duration of the test considerably.

The method for modeling presented herewith can be used to model the migration test. For the specific case of this test, some simplifications to the mathematical equations can be made. The migration tests are performed in saturated conditions, and no pressure gradient is applied on the liquid phase. In that case, the advection term in equation (14) can be dropped, as well as Richard's equation (equation 7). Furthermore, the saturated conditions allow to write:

$$\theta = \phi \quad (45)$$

$$\theta_s = 1 - \phi \quad (46)$$

where $\phi$ is the porosity of the material. Finally, the short duration of the test (about 120 hours), combined with the high velocity of the ions under the applied voltage, allow to neglect the chemical reactions between the ions and the hydrated paste of the material. Accordingly, the mass conservation equation (14) reduces to the extended Nernst-Planck equation:

$$\frac{\partial c_i}{\partial t} - \frac{\partial}{\partial t}\left(D_i \frac{\partial c_i}{\partial x} + \frac{D_i z_i F}{RT} c_i \frac{\partial \psi}{\partial x} + D_i c_i \frac{\partial \ln \gamma_i}{\partial x}\right) = 0 \quad (47)$$

Poisson's equation (2) is simplified to:

$$\tau \frac{d^2 \psi}{dx^2} + \frac{F}{\varepsilon}\left(\sum_{i=1}^{N} z_i c_i\right) = 0 \quad (48)$$

The flux of ion in the material is given as:

$$J_i = -\phi D_i \frac{\partial c_i}{\partial x} - \phi \frac{D_i z_i F}{RT} c_i \frac{\partial \psi}{\partial x} - \phi D_i c_i \frac{\partial \ln \gamma_i}{\partial x} \quad (49)$$

In equation (48) and (49), the diffusion coefficient $D_i$ is defined as:

$$D_i = \tau D_i^\mu \quad (50)$$

where $\tau$ is the tortuosity of the material and $D_i^\mu$ is the diffusion coefficient of the species i in free water, of values which can be found in physics handbooks. For example, the values of $D_i^\mu$ for the most common species found in cement-based materials are: $5.273 \times 10^{-9}$ m$^2$/s for OH$^-$, $1.334 \times 10^{-9}$ m$^2$/s for Na$^+$, $1.957 \times 10^{-9}$ m$^2$/s for K$^+$, $1.065 \times 10^{-9}$ m$^2$/s for SO$_4^{2-}$, $0.792 \times 10^{-9}$ m$^2$/s for Ca$^{2+}$, and $2.032 \times 10^{-9}$ m$^2$/s for Cl$^-$. These values are constant and represent the diffusion coefficients in very dilute conditions. The tortuosity appears in the model as a result of the averaging procedure. It accounts for the intricate path the ions travel through in a porous material. Equation (50) has very important implications. It shows, for instance, that if the diffusion coefficient $D_i$ of one ionic species is known, $\tau$ is also known and accordingly, the diffusion coefficient of the other ionic species are known. It also shows that as long as the tortuosity of the material remains unchanged, the $D_i$s remain constant.

Equation (47) is commonly used to model the migration test. But no reliable numerical solutions were available to solve it until recently. Accordingly, several simplifying assumptions have been used to solve this equation in order to analyze the results of migration tests. Two major trends are found in the literature: steady-state and non-steady-state analysis.

The assumptions underlying the steady-state analysis are given as follows. The steady-state is reached when the measured amount of chloride ions in the downstream cell varies linearly through time. This indicates a constant flux, which is the basic definition of the steady-state. The steady-state needs a very long time to be reached in classical diffusion test, but when the ions are accelerated with an external voltage, it is reached in a few days. During steady-state, all terms related to time in equation (47) are set to zero. This is equivalent to solving the flux equation (equation 49) with $J_i$ as a constant.

To further simplify the analysis, many authors have also assumed that the external voltage is strong enough to neglect the internal potential arising from the difference in the drift velocity of the various ionic species. This hypothesis allows to write:

$$\frac{\partial \psi}{\partial x} = \frac{\Delta \psi_{est}}{L} = -E_{ext} = \text{constant} \quad (51)$$

where $\Delta \psi_{ext}$ is the applied voltage difference across the sample, L is the thickness of the specimen, and $E_{ext}$ is the corresponding constant electric field. It is also assumed that the applied voltage is strong enough to neglect diffusion. Finally, the chemical activity is dropped from the analysis. In that case, equation (49) reduces to:

$$J_i = -\phi \frac{D_i z_i F}{RT} c_i \frac{\Delta \psi_{ext}}{L} \quad (52)$$

where $J_i$ is a constant since steady-state is reached.

Another way to analyze the migration test is through a non-steady-state (or transient) analysis. In this case, one of the main assumption is that the chemical reactions can be neglected. Tests performed in transient state are rather short and, combined with the high velocity of the ions under the applied field, the chemical reactions allegedly do not have time to have a significant effect on the ionic transport. Neglecting the chemical reactions also implies that there is no change to the microstructure of the paste during the duration of the test, which allows to consider the porosity and tortuosity as constants. As for the steady-state analysis, the external potential is assumed to be much stronger than its internal counterpart. The effect of the chemical activity is also neglected. With all these hypothesis, equation (47) reduces to:

$$\frac{\partial c_i}{\partial t} - \frac{\partial}{\partial t}\left(D_i \frac{\partial c_i}{\partial x} + \frac{D_i z_i F}{RT} c_i E_{ext}\right) = 0 \quad (53)$$

and can be solved analytically. For semi-infinite media, the analytical solution of equation (53) with a constant $D_i$ is:

$$c = \frac{c_o}{2}\left[\text{erfc}\left(\frac{x}{2\sqrt{D_i t}} - \frac{z_i F E_{ext} \sqrt{D_i t}}{2RT}\right) + e^{\left(\frac{z_i F E_{ext}}{RT} x\right)} \text{erfc}\left(\frac{x}{2\sqrt{D_i t}} + \frac{z_i F E_{ext} \sqrt{D_i t}}{2RT}\right)\right] \quad (54)$$

where $c_o$ is the boundary condition at $x=0$. To obtain the diffusion coefficients with this model, a $D_i$ is fitted to chloride profiles measured on the samples undergoing the migration test.

Figure 3:
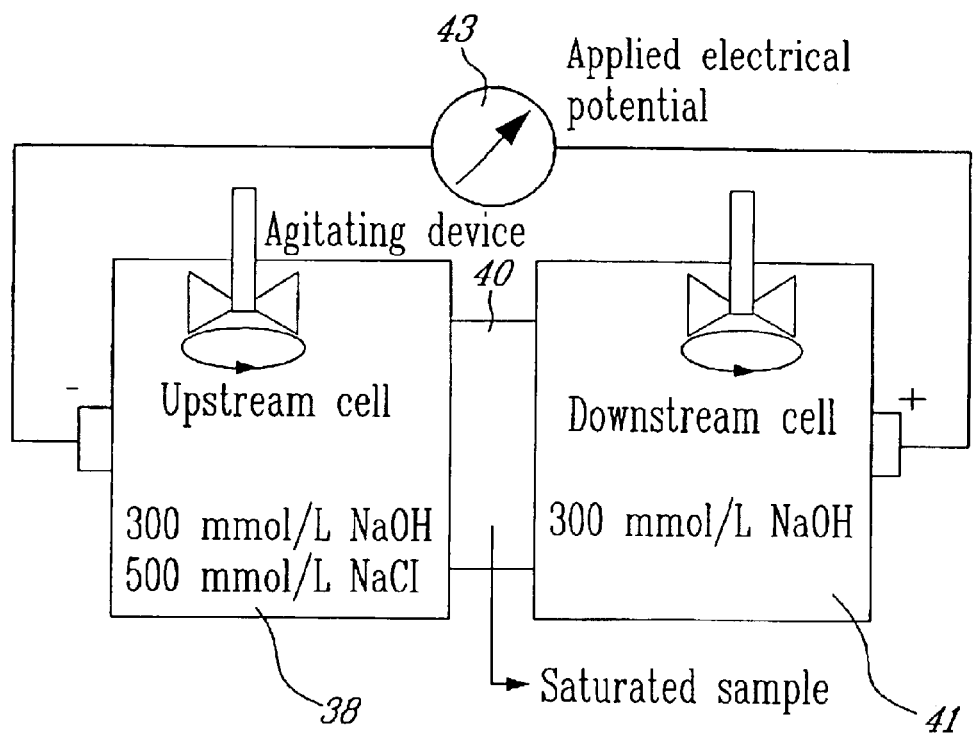
FIG. 3 illustrates a typical setup for the migration test.
Figure 4:
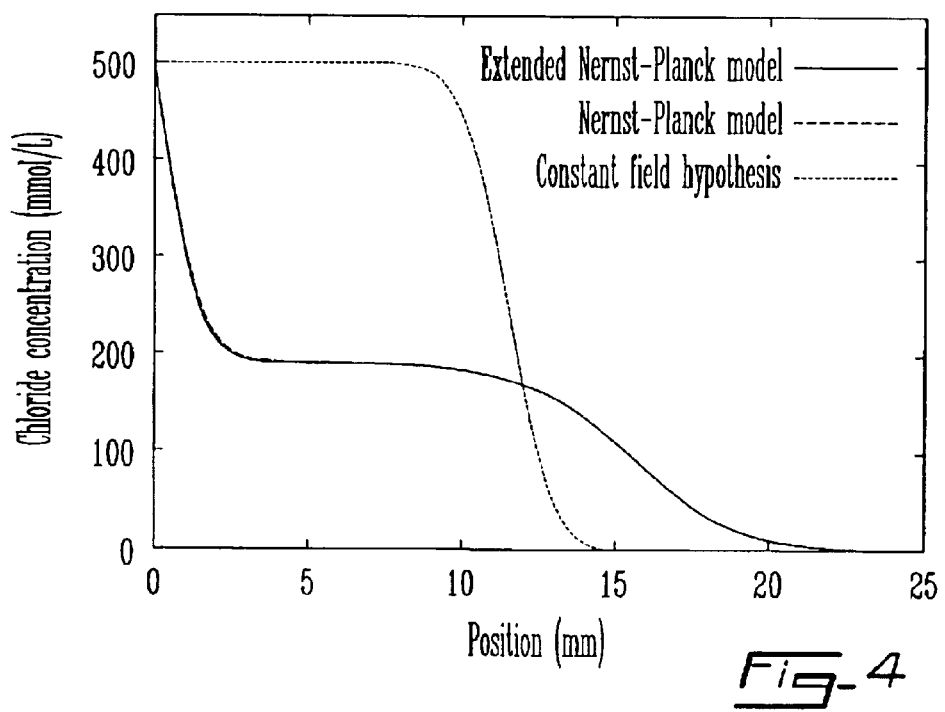
FIG. 4 is a graph of the chloride concentration (mmol/L) versus the position (mm) in a sample problem. It gives the chloride concentration profiles after 10 hours when the internal potential is either considered or not.

Both methods (steady-state and transient), are based on the hypothesis that the electrical coupling between the ions can be neglected when an external potential is applied. To verify the validity of this hypothesis, a sample problem is considered. The problem will be solved with and without the constant field hypothesis to see if the latter can be used in the analysis of the migration test. A cement-based material with a tortuosity of $\tau=1/100$ and a porosity of 30% is assumed. According to equation (50), the diffusion coefficient of each ionic species is: $5.273 \times 10^{-11}$ m$^2$/s for OH$^-$, $1.334 \times 10^{-11}$ for Na$^+$, $1.957 \times 10^{-11}$ for K$^+$, $1.065 \times 10^{-11}$ for SO$_4^{2-}$, $0.792 \times 10^{-11}$ for Ca$^{2+}$, and $2.032 \times 10^{-11}$ for Cl$^-$. The sample has a 25 mm thickness and is subjected to a 10V applied potential (this corresponds to a 400 Volt/m electrical field). The boundary conditions correspond to the typical setup as shown in FIG. 3, i.e. OH$^-$=300, Na$^+$=800, and Cl$^-$=500 mmol/L at $x=0$, and OH$^-$=300 and Na$^+$=300 mmol/L at $x=25$ mm. All of the other concentrations are set to zero on both ends of the material. Finally, the initial concentrations in the sample are: OH$^-$=354.0, Na$^+$=250.0, K$^+$=120.0, SO$_4^{2-}$=10.0, Ca$^{2+}$=2.0 and Cl$^-$=0.0 mmol/L. The initial potential is zero everywhere in the material. A temperature of 25° C. is assumed. The chloride concentration profiles after 10 hours are shown in FIG. 4. The huge difference between the solution of the extended Nernst-Planck model and the model with the constant electrical field shows that the fact of neglecting the internal potential when modeling a migration test can lead to very misleading results with regard to the chloride profiles, and accordingly to the ionic flux evaluation (see equation 49).

The latter results lead to the development of a new method to analyze the migration test. The new method proposed to evaluate the diffusion coefficients is based on non steady-state current measurements. The boundary conditions correspond to the concentrations in both cells as well as the imposed potential difference over the sample. The initial conditions are given by the concentrations of the ions in pore solution prior to the test. With these data, the equations are solved with different tortuosity values according to the numerical method presented in the preceding section. The numerical current $I_c^{num}$ is calculated at the measurement times according to:

$$I_c^{num} = SF \sum_{i=1}^{N} z_i J_i \qquad (55)$$

where S is the exposed surface of the sample and $J_i$ is the ionic flux given by equation (49). For each tortuosity value, the error between the model and the measurements is calculated as:

$$\text{error} = \sqrt{\sum_{k=1}^{M} (I_{c,k}^{mes} - I_{c,k}^{num})^2} \qquad (56)$$

where M is the total number of measurement and $I_c^{mes}$ and $I_c^{num}$ are the measured and numerical currents. The tortuosity value leading to the smallest error with the measurements gives the proper diffusion coefficients for each ionic species in the material considered.

Figure 19:
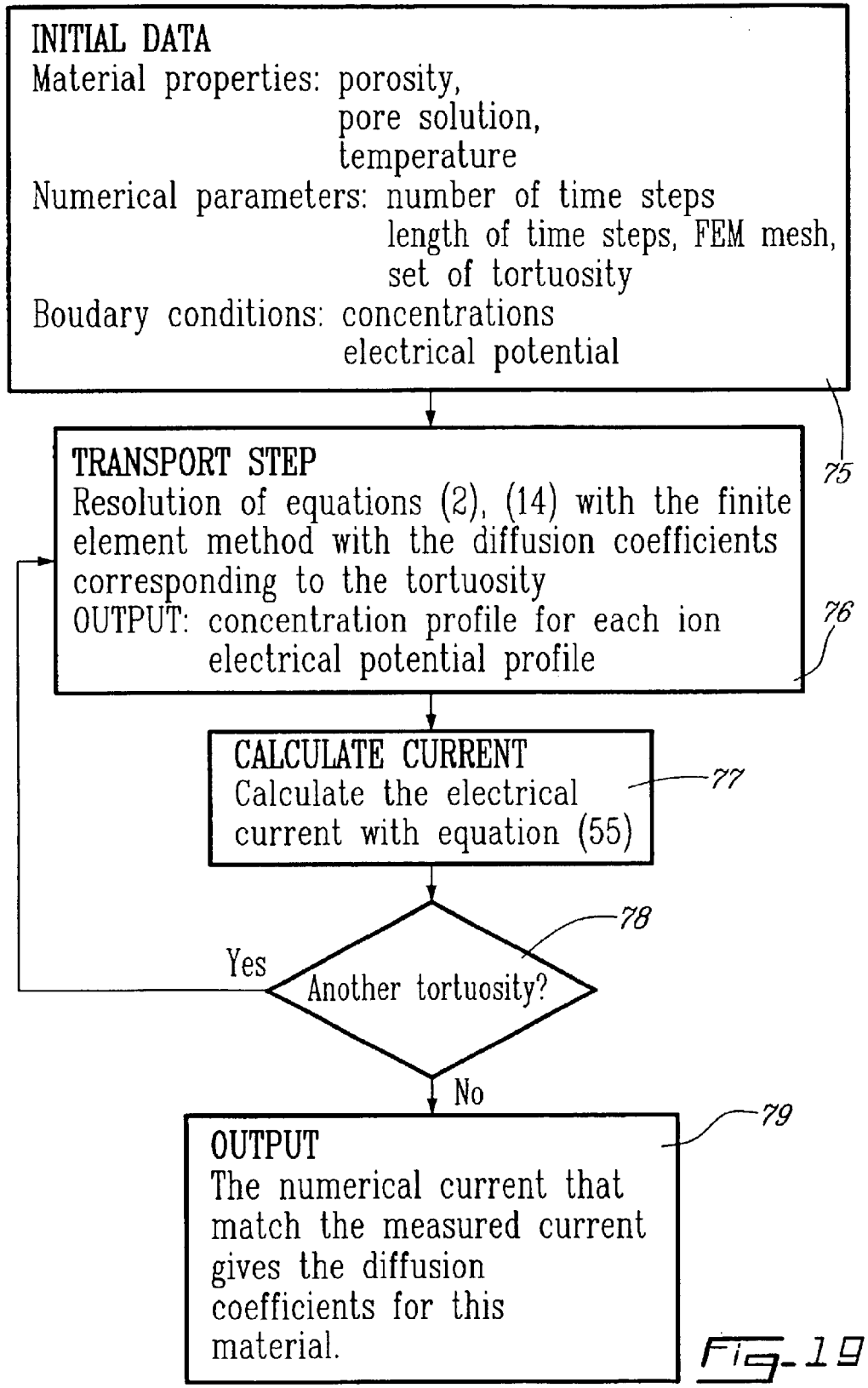
FIG. 19 is a flow chart of an overview of another preferred algorithm according to the invention.

This other preferred embodiment is summarized in FIG. 19. The calculation starts from input data giving the material properties, numerical parameters and boundary conditions 75. The material properties can be the porosity, the temperature, ionic pore solution. The boundary conditions can be the concentrations and the electrical potential. The numerical parameters can be the number of time steps and their length, the finite element mesh and the set of tortuosity.

The invention first performs a transport step 76, in which the concentration profile for each ion and the electrical potential profile are determined using the diffusion coefficients corresponding to the first tortuosity.

It will be readily understood by one skilled in the art that in order to solve the transport equations, any numerical method could have been used. The preferred numerical method for solving the transport equations is the finite elements method. However, the finite differences and the finite volumes methods could be used without departing from the present invention.

Then, a step of calculation of the current 77 follows. The electrical current is determined for each tortuosity.

The transport step 76 and the current calculation step 77 are repeated for each tortuosity parameter until a numerical current matching a measured current is found which will give the diffusion coefficients for the material.

Figure 20:
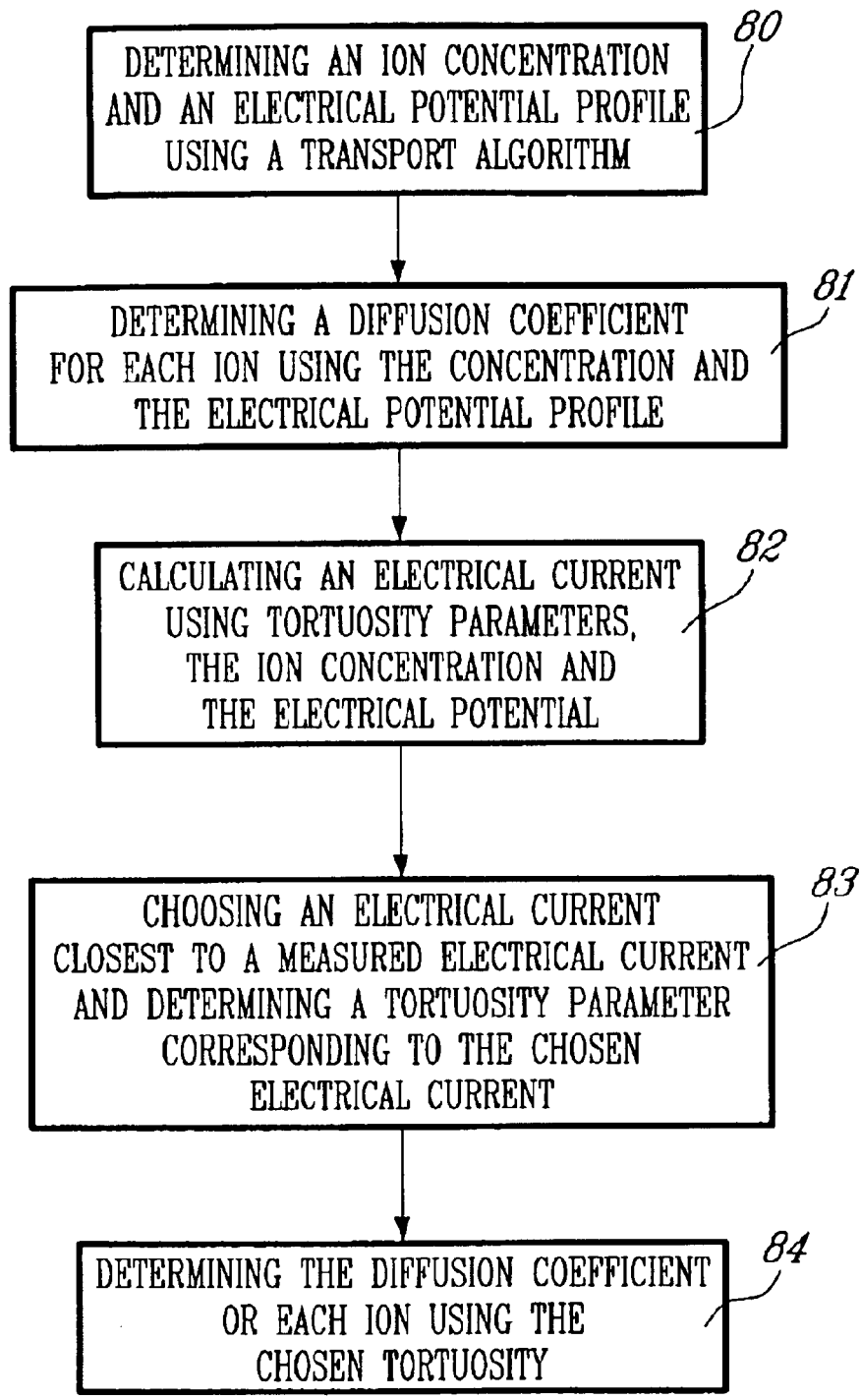
FIG. 20 is a flow chart of the main steps of another preferred embodiment of the present invention.

FIG. 20 is a flow chart of the main steps of this preferred embodiment of the present invention. The preferred embodiment is a method for determining an ion diffusion coefficient for each of at least two ions capable of undergoing transport in a cement-based material. The method comprising the steps of: determining a concentration 80 for each the ions and an electrical potential profile using a transport algorithm and determining a diffusion coefficient 81 for each ion using the concentration and the electrical potential profile.

Preferably, the method further comprises calculating 82 a set of electrical currents, each electrical current corresponding to one tortuosity parameter using the concentration, the electrical potential and the tortuosity parameter; choosing 83 an electrical current from the set with a value closest to the measured electrical current and determining a matching tortuosity parameter corresponding to the chosen electrical current and determining 84 the diffusion coefficient for each ion using the matching tortuosity.

FIRST EXAMPLE

Description of the Problem

The first example concerns the prediction of the behavior of a concrete slab undergoing external sulfate attack. This type of attack is characterized by the penetration of sulfate (SO$_4^{2-}$) in the material, which precipitates into ettringite and gypsum. The formation of these two phases leads to microcracking of the cement paste. The invention allows to locate the ettringite and gypsum through time, giving valuable information on the degradation state of a structure. Parallel to this, the leaching of OH$^-$ and Ca$^{2+}$ out of the material leads to the dissolution of portlandite and the decalcification of C—S—H, which weaken the structure. Again, the invention allows to track the dissolution fronts of both of these phases.

Figure 5:
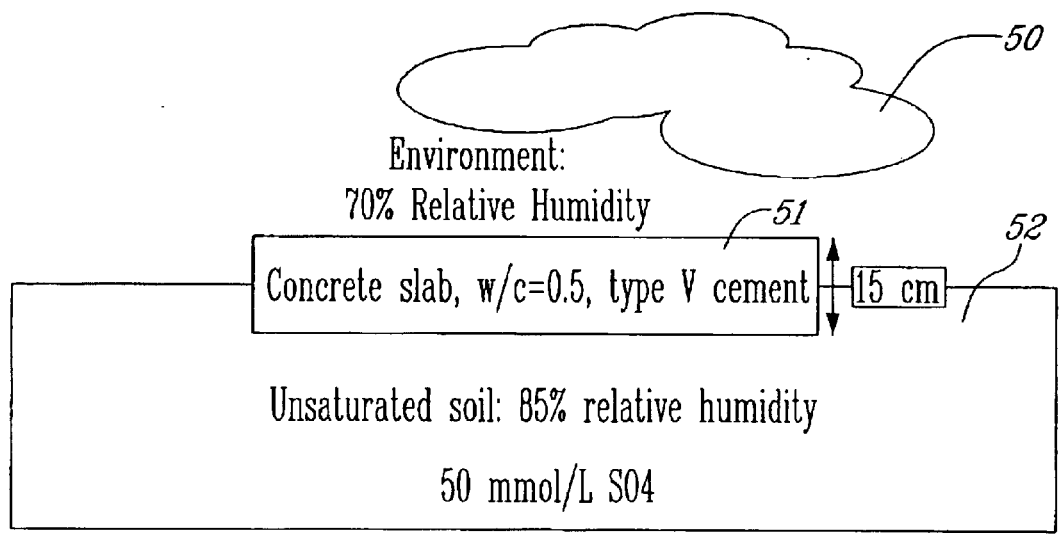
FIG. 5 is an illustration of the setup for the case considered for the numerical simulations.

The case considered for the numerical simulations is shown in FIG. 5. It consists of a 15 cm thick concrete slab S1 lying on a soil S2 bearing a high concentration of sodium sulfate. The concrete S1 has a water/cement ratio of 0.50 and is made with an ASTM type V cement. The soil S2 on which the slab lies is at a relative humidity of 85%. The external environment 50, in contact with the upper part of the slab, is at a relative humidity of 70%. This gradient in relative humidity will create a flow of water directed upward that will contribute, along with diffusion, to move the SO$_4^{2-}$ ions into the material. Besides SO$_4^{2-}$, five other ions are considered in the simulations: OH$^-$, Na$^+$, K$^+$, Ca$^{2+}$, and Al(OH)$_4^-$.

The boundary conditions are as follows. On the lower part of the slab S2 (x=0), a concentration of 5000 ppm of SO$_4^{2-}$ is imposed, which corresponds roughly to 50 mmol/L. Accordingly, a concentration of 100 mmol/L of Na$^+$ is set at x=0. The concentration of all other species at x=0 is zero. On the upper part of the slab S2 (x=0.15), there is no transfer of ions from the material to the environment. This boundary thus acts as a barrier for the ions. Consequently, a null flux is imposed (natural boundary conditions).

Figure 6:
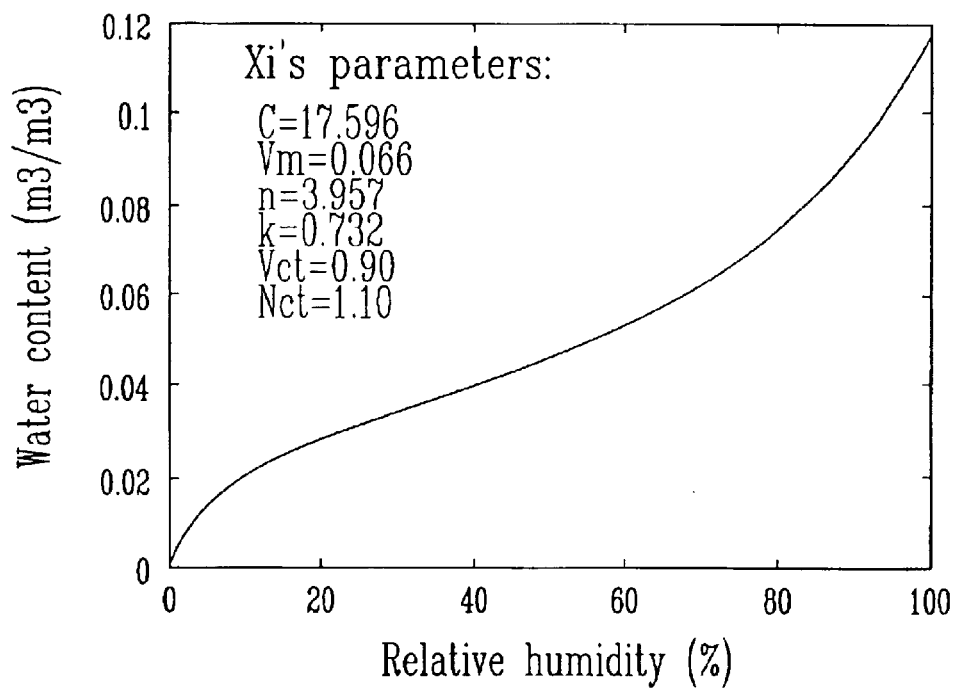
FIG. 6 is an illustration of the water content versus the relative humidity (%) for the adsorption isotherm according to Xi's model.

The imposition of the boundary conditions for the water content θ is more complicated. It was mentioned that the soil S2 is at an 85% relative humidity and that the environment 50 is at 70%. To convert these values in water content, the water adsorption isotherm model is used, which gives the nonlinear relationship between θ and the relative humidity in the material (see FIG. 6). According to this model, an 85% relative humidity corresponds to a 0.0823 m$^3$/m$^3$ water content, and a 70% relative humidity corresponds to 0.0626 m$^3$/m$^3$. These values are imposed at x=0 and x=0.15 respectively.

For the electrical potential ψ, a reference value must be set at some point. A value of zero is thus imposed at x=0.

The initial concentration in the pore solution of the material is given in Table 2. It was evaluated with the chemical equilibrium code developed by Reardon in "An ion interaction model for the determination of chemical equilibria in cement/water systems", Cement and Concrete Research, vol. 20, p. 175–192, 1990. The initial value of the water content is 0.0858 m$^3$/m$^3$, which corresponds to a relative humidity of 87% in the material. Finally, the initial value of the potential is zero throughout the slab.

TABLE 2

Data for the numerical simulations - First example

| Properties | Value | Properties | Value |
|---|---|---|---|
| Cement type | V | Cement composition | (%) |
| w/c | 0.50 | C$_3$S | 56.31 |
|  |  | C$_2$S | 22.04 |
|  |  | C$_3$A | 1.69 |
|  |  | C$_4$AF | 11.26 |
| Concrete mixture | (kg/m$^3$) | Initial solid phases | (g/kg) |
| Cement | 342.5 | C—S—H | 89.4 |
| Water | 171.3 | Portlandite | 44.8 |
| Aggregates | 1944.0 | Ettringite | 14.6 |
| Density | 2457.8 | Hydrogarnet | 11.1 |
| Initial pore solution | (mmol/L) | Diffusion coefficients | (m$^2$/s) |
| OH$^-$ | 626.0 | OH$^-$ | 2.03 × 10$^{-10}$ |
| Na$^+$ | 204.1 | Na$^+$ | 5.13 × 10$^{-11}$ |
| K$^+$ | 475.8 | K$^+$ | 7.53 × 10$^{-11}$ |
| SO$_4^{2-}$ | 28.0 | SO$_4^{2-}$ | 4.10 × 10$^{-11}$ |
| Ca$^{2+}$ | 1.1 | Ca$^{2+}$ | 3.05 × 10$^{-11}$ |
| Al(OH)$_4^-$ | 0.1 | Al(OH)$_4^-$ | 2.08 × 10$^{-11}$ |
| Rel. humidity (%) | (m$^3$/m$^3$) | Water diffusivity | (m$^2$/s) |
| 70 | 0.0626 |  | 2.72 × 10$^{-12}$e$^{81.2\theta}$ |
| 85 | 0.0823 |  |  |
| 87 | 0.0858 |  |  |
| Porosity | 0.118 | R | 8.3143 J/mol/° K |
| T | 25° C. | $\epsilon$ | 6.94 × 10$^{-10}$ C/V/m |
| F | 96488.46 C/mol | $\tau$ | 0.038 |
| e$_o$ | 1.602 × 10$^{-19}$ C |  |  |

All the other parameters and characteristics of the material are given in Table 2. The initial distribution of solid phases is calculated by considering the hydration reactions of cement. It is assumed that the paste is fully hydrated at the beginning of the simulations. The porosity is evaluated from data on hydrated cement pastes found in Taylor H. F. W., "Cement chemistry", Academic Press (Canada), 1990. The diffusion coefficient values are based on results of chloride migration experiments. These values are used to evaluate the tortuosity $\tau$, which is given by the diffusion coefficient of a given species in the material ($D_i$) divided by its value in free water ($D_i^{\prime\prime}$). Taking for example OH$^-$, $D_i$ is 2.03×10$^{-10}$ m$^2$/s and $D_i^{\prime\prime}$ is 5.273×10$^{-9}$ m$^2$/s, which yields a tortuosity of 0.038. The adsorption of ions is neglected in this example.

The only parameters not yet discussed related to the movement of water in the pore system under capillary effects. As seen in equations (7) and (14), two parameters are needed: $D_\theta$ and $D_L$. However, it was shown that for high values of relative humidity, such as in the present example, $D_\theta \approx D_L$. Hence, only the value of $D_L$ is needed. Based on NMR imaging of water absorption in mortars, this nonlinear parameter is taken as $D_L = 2.72 \times 10^{-12} e^{81.2\theta}$.

Before showing any simulation results, note on the ability of the chosen algorithm to handle the water flowing through the material as a result of capillary suction. To have an idea of the relative importance of the flow with regards to diffusion, the Peclet number ($P_e$) for the material properties mentioned previously is calculated. $P_e$ is given by VL/D, where V is the velocity of the flow, L is the length of the domain and D is the diffusion coefficient. In the present case, V can be calculated with equation (8), with the gradient of water content evaluated from the analytical solution of equation (7) in steady-state. It gives 1.42×10$^{-10}$ m/s, corresponding to a water flux of 12.3 ml/day/m$^2$. Since multiple ions are considered, one species must be selected in order to calculate $P_e$. The diffusion coefficient of OH$^-$, which is 2.03×10$^{-10}$ m$^2$/s is chosen. This results in a Peclet number of 0.11, which is low. The problems commonly associated with convection-dominated problems, like strong oscillations, are not likely to occur at such low values of $P_e$. Even for a very high gradient of relative humidity such as 95%–60%, $P_e$ is 0.7, still well below values expected to lead to numerical oscillations.

But still, two types of problem occur. For the particular case of a concrete slab S2 exposed on its upper surface to the environment, the natural boundary condition at this location prevents the ions from exiting the slab S0. Combined with the upward water flux, it means that the ions tend to accumulate in the upper part of the slab. In the case of a sulfate attack, this is particularly true for Na$^+$ and SO$_4^{2-}$ since they are present in the groundwater. This can lead to very high concentration gradients at x=L, and consequently to divergence of the algorithm. Numerical tests have shown that at some point, the concentrations in Na$^+$ and SO$_4^{2-}$ may reach such high levels that even increasing the number of elements in this region cannot prevent the algorithm to crash. Taking the formation of mirabilite into account in the model helps to prevent this situation since it absorbs a large amount of Na$^+$ and SO$_4^{2-}$ ions.

The other problem caused by the presence of moisture transport in the model occurs in the first time steps. Starting from an initial water content level, imposing Dirichlet-type conditions may lead to numerical oscillations near the boundaries because of initially high gradients in these areas. In a classical diffusion problem, these oscillations would tend to disappear with time. With the current model, however, they must be avoided. Since the concentration is coupled to the water content, oscillations in the latter can induce oscillations in the ionic profiles. The problem is that if the oscillations are such that they lead to negative concentrations at some nodes, the chemical equilibrium module will not be able to find a solution since negative concentration do not make physical sense. To avoid this problem, one solution consist in increasing the number of nodes near the boundaries, to avoid, as much as possible, the oscillations. Another solution is to gradually impose the boundary conditions for the water content over time, which is similar to the incremental load method commonly used in solid mechanics. This technique proved successful to avoid the problems related to the oscillations in the water content profiles. Finally, if the initial humidity in the material is lower than 100%, oscillations may not be a problem. With the data proposed in Table 2, i.e. a 87% RH initial material exposed to a 85%–70% RH gradient, none of the previously exposed problems happens.

In this example, the simulations are performed over a period of twenty years. The domain is discretized with 50 elements of equal length. The time steps are one day long.

Results and Discussion

Figure 7:
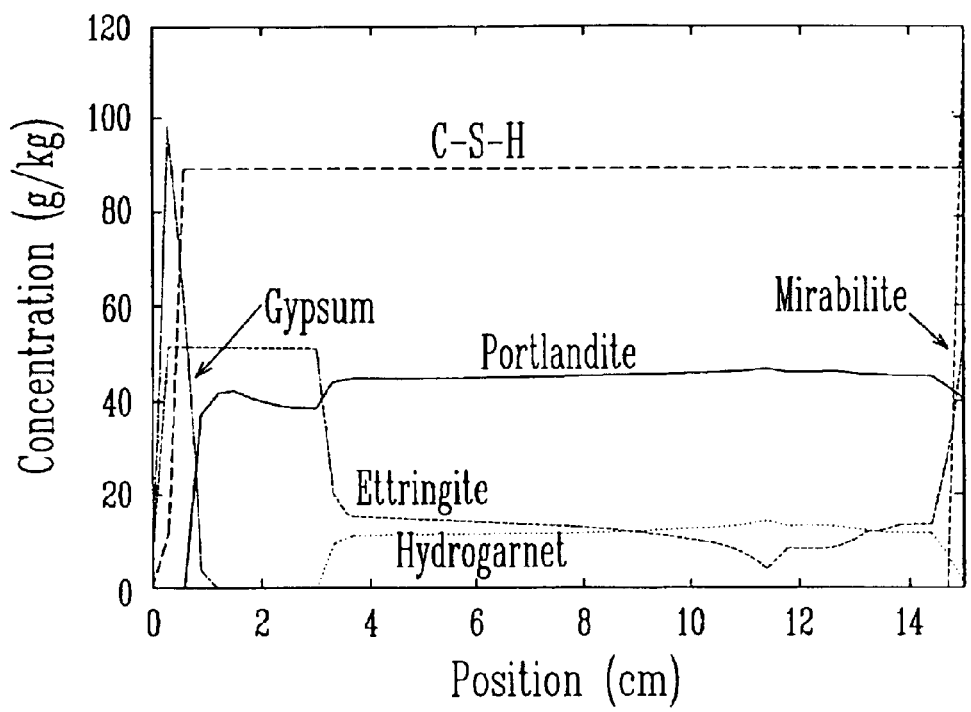
FIG. 7 is an illustration of the concentration (g/kg) versus the position (cm) for the solid phase distribution after 20 years.

The solid phase distribution is shown in FIG. 7. One of the main effect of the penetration of sulfates in the material is the formation of an ettringite front that proceeds toward the top of the slab. It is located at 3 cm from the exposed surface after 20 years. It is accompanied by a narrow peak of gypsum that forms near the bottom part of the slab, between 0 and 1 cm. Since calcium ions are necessary to form ettringite, it can be seen that a small portion of portlandite, whose position matches with the front of ettringite, was dissolved in order to achieve that. Also matching the position of the ettringite front is the dissolution of hydrogarnet, whose $Ca^{2+}$ and $Al(OH)_4^-$ are used to form ettringite. When the hydrogarnet is totally dissolved, no further amount of alumina is available, which explains that the formation of ettringite reaches a maximum. It must be noted that ettringite also precipitates near the upper surface of the slab. Finally, portlandite is completely dissolved between the exposed surface and 0.5 cm, while only a small amount of C—S—H is decalcified.

Since it is assumed that there are no $Ca^{2+}$ and $OH^-$ ions in the soil, they tend to leach out of the material. This leads to a dissolution of portlandite and a decalcification of C—S—H. Again, these chemical reactions tend to progress upward. The numerical results clearly show that the dissolution of portlandite occurs before the decalcification of C—S—H, an observation also made in experimental tests.

Finally the results show the formation of mirabilite on the upper part of the material. It is caused by the accumulation of $Na^+$ and $SO_4^{2-}$ ions in this region, as a result of the flow of water directed upward. This result makes sense since the upper part of the slab is the only place in the material where the $Na^+$ and $SO_4^{2-}$ ions can accumulate and reach the concentration level necessary to precipitate. The precipitation of ettringite at this location may also be an effect of the upward water flow.

Figure 8:
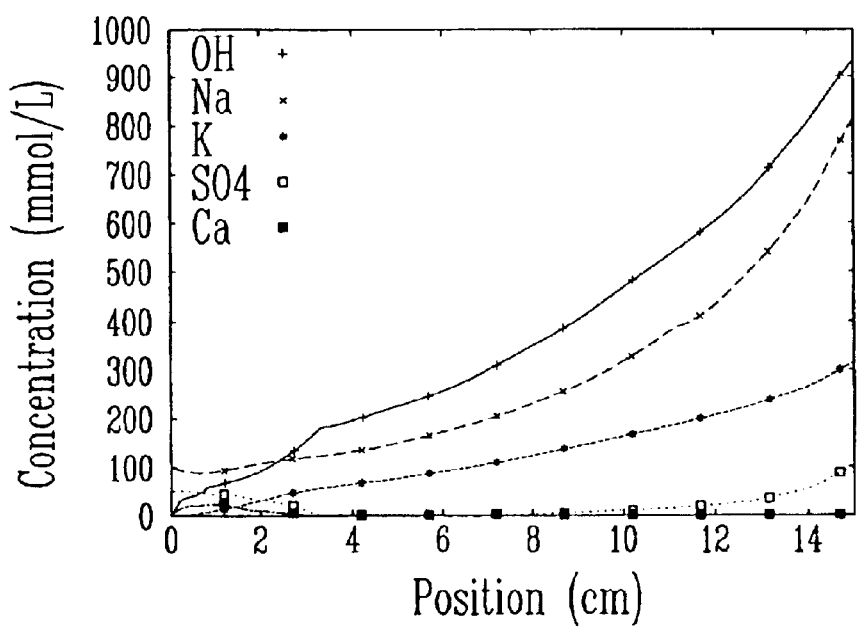
FIG. 8 is an illustration of the concentration (mmol/L) versus the position in (cm) of a few ionic species and their distribution after 20 years.

FIG. 8 shows the distribution of ions after ten years. The profile of $Al(OH)_4^-$ is not shown since its concentration values are very small. A verification made after the calculation showed that the ionic concentrations at a given nodes are in equilibrium with the solid phases found at this particular location.

Figure 9:
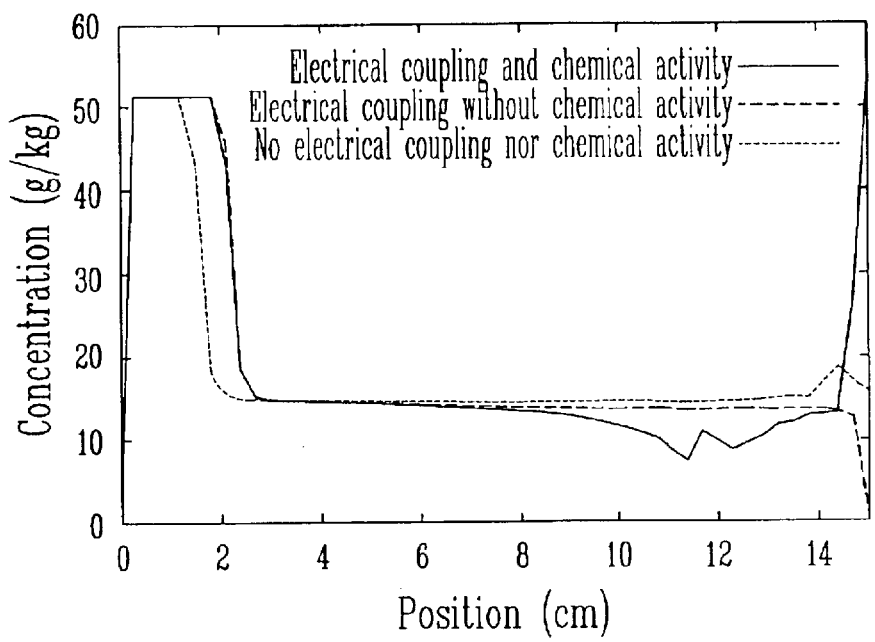
FIG. 9 is an illustration of the concentration (g/kg) versus the position (cm) for the comparison of the ettringite front after 10 years between the complete model and the cases where the electrical coupling and/or chemical activity effects are neglected.

Simulations were performed without the electrical coupling and the chemical activity effect to weigh their effect on the overall result. The comparison with the previous result is shown on FIG. 9. Neglecting the chemical activity effects does not seem to have an important effect on the ettringite front. Yet, the model does not predict the formation of ettringite at the surface (x=0.15) when the influence of chemical activity is not considered. So obviously, chemical activity is an important part of the process and should be considered. When the electrical coupling is also neglected, the difference in the position of the ettringite front is important. This shows the importance of considering both the electrical coupling and the chemical activity.

Figure 10:
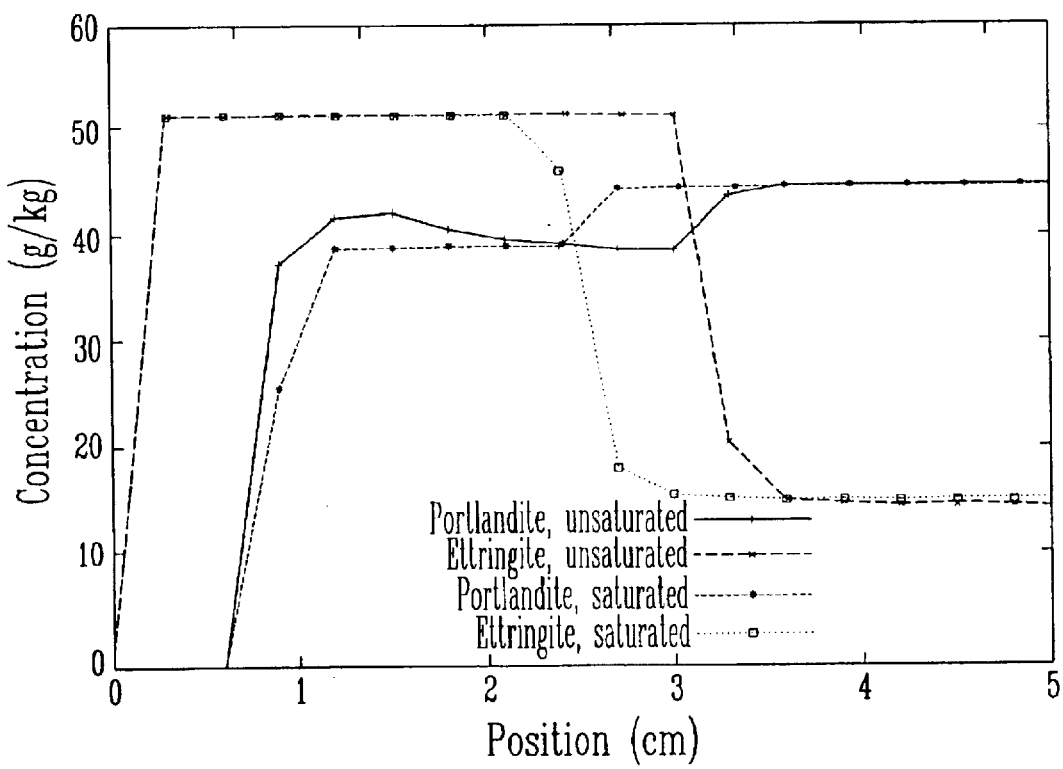
FIG. 10 is an illustration of the concentration (g/kg) versus the position (cm) for the comparison of the ettringite and the portlandite profiles after 20 years for the saturated and unsaturated cases.

The next results show the effect of the capillary suction on the solid phase distribution. FIG. 10 compares the ettringite and portlandite profiles for the saturated and unsaturated cases. The simulation for the saturated case was performed with an initial water content in the material that is equal to the porosity, meaning that all of the porous space is filled with water. The boundary conditions for the water content also corresponds to the porosity for both ends of the slab. All of the other boundary conditions as well as all of the other parameters are the same as for the previous simulations. The results show that the ettringite fronts penetrates less in the material when it is saturated. It clearly emphasizes the effect of the upward water flow caused by capillary suction on the sulfate ions, that go farther in the concrete in that case. The difference between the portlandite profiles is very slight. Nevertheless, one can see that the degradation of portlandite is less important for the unsaturated case. It shows that the upward flow of water tends to slow the downward leaching of $Ca^{2+}$ and $OH^-$ ions, thus slowing the dissolution of portlandite. Simulations have shown that the effects on both the ettringite and the portlandite described above are more important as time increases.

Figure 11:
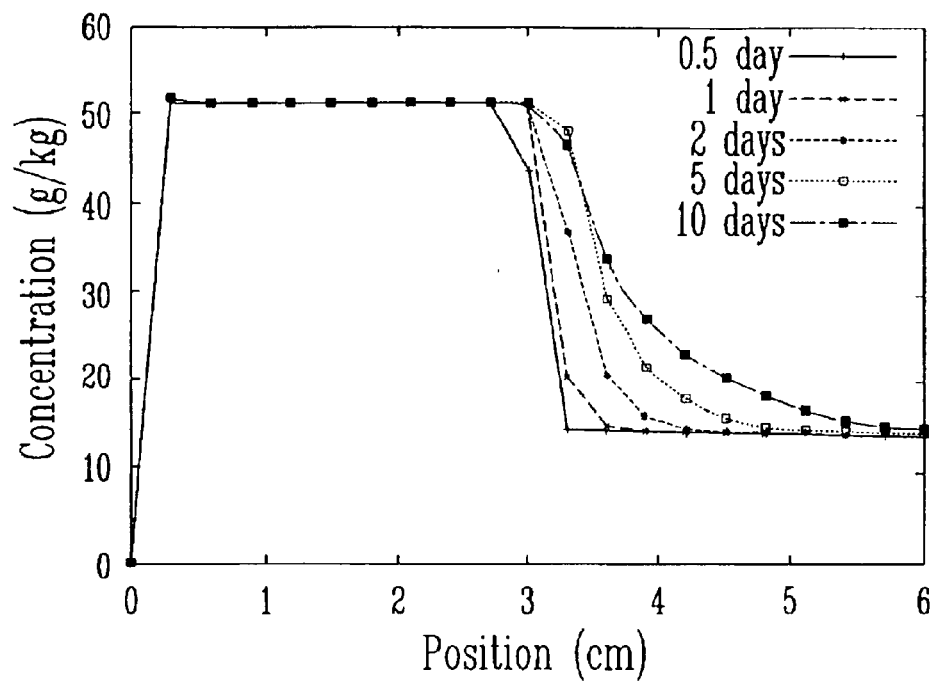
FIG. 11 is an illustration of the concentration (g/kg) versus the position (cm) for the effect of the size of the time steps on the ettringite profile at 20 years.

It was mentioned earlier that the algorithm needs small time steps in order to perform properly. The next simulations were performed to measure the effect of different time steps on the solution. FIG. 11 shows the ettringite profile after twenty years obtained through time steps of 0.5, 1, 2, 5, and 10 days. It shows that as the time steps is increased, the ettringite front is less and less sharp. Thus, the time step clearly has an influence on the shape of the profile, with a smaller time step meaning sharper, more precise solid phase profiles. As the time steps are getting smaller, the difference between each solution reduces, ultimately converging toward a unique solution. In FIG. 11, the difference between the solution with $\Delta t=1$ day and $\Delta t=0.5$ day is very small, so the one day time step is sufficient to reliably perform the simulation.

Figure 12:
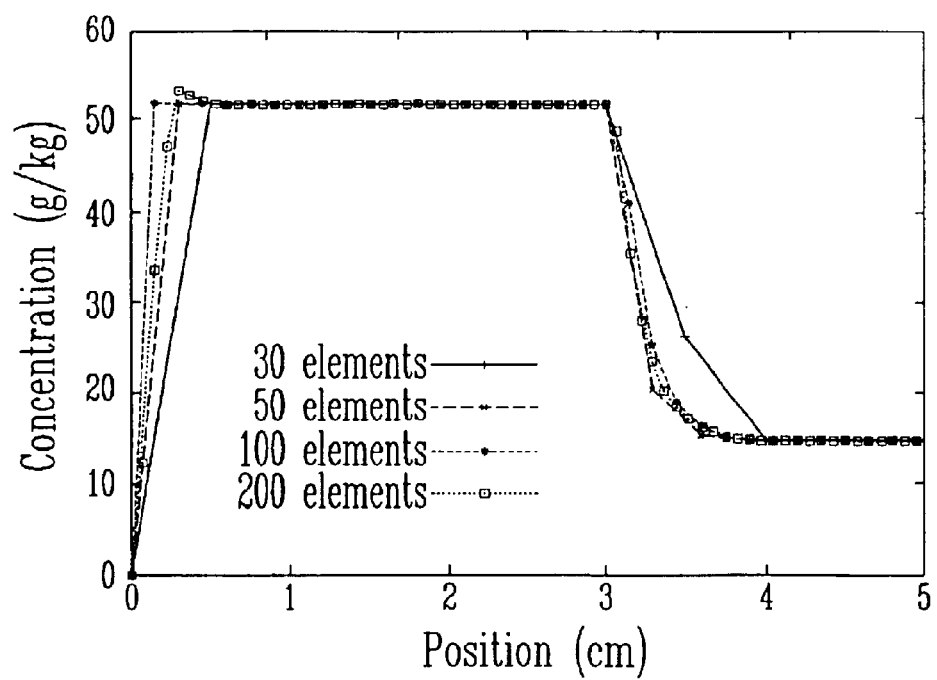
FIG. 12 is an illustration of the concentration (g/kg) versus the position (cm) for the effect of the number of elements on the ettringite profile at 20 years.

The same kind of simulation was performed but this time with a different number of elements. The results are given in FIG. 12 for 30, 50, 100 and 200 elements, again for the ettringite phase. The profiles show some differences near the boundary x=0. However, this is simply a discretization effect. For all cases, there is no ettringite on the first node, and it reaches its maximum value on the next node. What is more interesting is the solution at the position of the ettringite front. The solution is almost identical, whatever the number of elements, except maybe for the case with 30 elements. Even in that case, the difference is not very important compared to those obtained with different time steps. It means that the choice of element should be made in order for the transportation part of the algorithm to converge. This choice has virtually no influence on the shape of the solid phase profiles.

SECOND EXAMPLE

Description of the Problem

Figure 13:
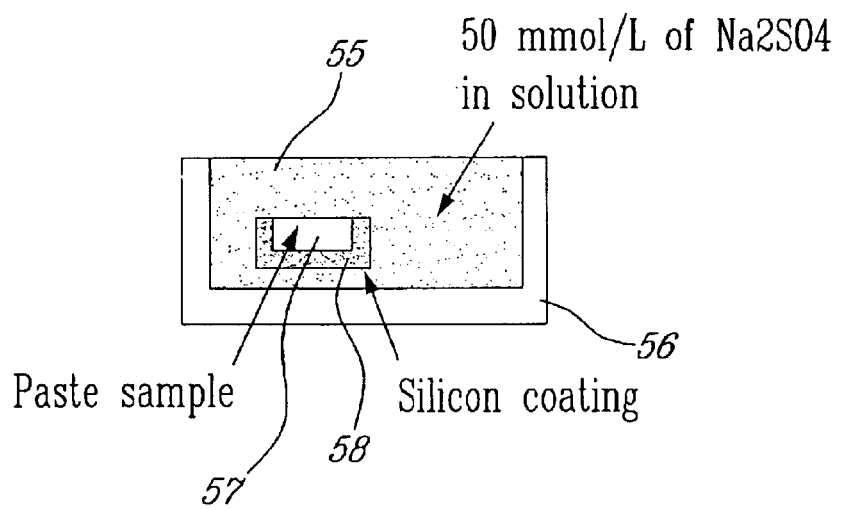
FIG. 13 is an illustration of the experimental setup for the degradation of a cement paste exposed to $Na_2SO_4$ solution.

The model can be used to predict the degradation of various cement-based materials (pastes, mortars, concretes) exposed to aggressive chemical solutions. It is used herein to analyze the behavior of cement paste disks made of an ordinary Portland cement prepared at a water/cement ratio of 0.60. The paste was cured for a year in aluminum foil. It was then cut in 12 mm disks. As shown in FIG. 13 these samples 57 were immersed for three months in a sodium sulfate solution 55 prepared at a concentration of 50 mmol/L. All sides of the sample except one were coated with silicon 58. The material being exposed to the aggressive solution on only one face ensures a one-dimensional process. In order to maintain constant the boundary conditions during the test, the test solution was regularly renewed. The microstructural alterations were investigated by means of electron microprobe analyses and scanning electron microscopy.

The various characteristics of the material are given in Table 3. The initial solid phases forming the cement paste are calculated by considering the hydration reactions of cement. The results are adjusted to take into account the one-year curing time. All of the $SO_3$ present in the cement reacts with the $C_3A$ to form the initial amount of ettringite. The remaining part of the $C_3A$ as well as the $C_4AF$ react with water to yield hydrogarnet. Following microscope observations, it is assumed that only 35% of $C_4AF$ reacts.

The initial pore solution is obtained according to the pore solution extraction procedure. Samples were placed in an extraction cell and crushed at a pressure of approximately 300 MPa. Typically, 2 to 5 ml of pore solution are extracted. The solution is delivered through a drain ring and channel, and recovered with a syringe in order to limit exposure to the atmosphere. Chemical analyses of the pore solution were carried out shortly after the extraction test. The composition of the solution was then adjusted in order to respect the electroneutrality condition. Slight deviations from electroneutrality can arise due to the experimental error associated with the evaluation of the ionic concentrations. The neutral solution is once again corrected so that the concentrations of the species are in accordance with the chemical equilibrium constants displayed in Table 1. This correction is performed with the chemical equilibrium code described previously.

The porosity is calculated according to the standardized ASTM C642 water porosity procedure.

Figure 14:
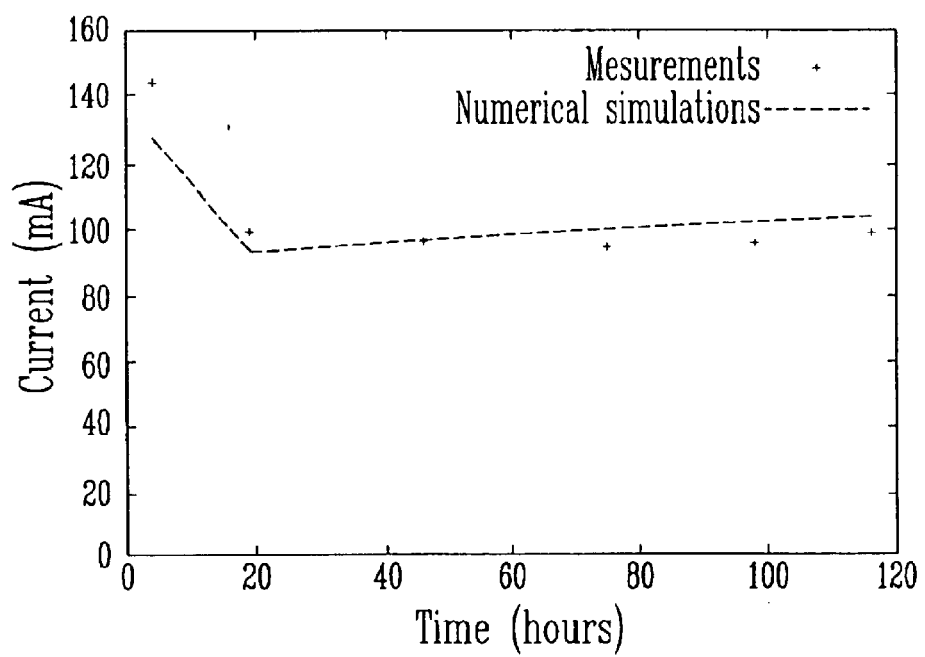
FIG. 14 is an illustration of the current (mA) versus the time (hours) for the reproduction of the measured currents during the migration test with the second embodiment of the invention.

The diffusion coefficient of each ionic species is evaluated according to the procedure detailed in the second embodiment of the invention. The upstream and the downstream cells of the migration setup both contain a 300 mmol/L NaOH solution. The upstream cell also contains a 500 mmol/L NaCl solution. Two disks are tested. They are about 25 mm thick with an exposed surface of approximately 75 mm. They were both vacuum saturated for 24 hours prior to the test. A 5 Volt potential difference is applied to the sample for the full duration of the test. Electrical current through the setup is measured for four days (90 hours). A preferred embodiment of the invention is then used to reproduce the measured currents. The thickness of the sample is discretized with 200 elements. The mesh is refined in a 2 mm layer on both extremities of the domain, where 50 elements are used. The simulations with various values of $\tau$ are performed with 90 time steps of one hour each. The value of $\tau$ that offers the best match with the measured current curve yields the diffusion coefficients for that particular material. This best-fitting curve is shown in FIG. 14 for one of the disks. A similar curve is obtained for the other disk. The diffusion coefficients shown in Table 3 correspond to the average values for the two sets of measurements. The corresponding tortuosity value is also indicated in Table 3.

This example occurs in saturated conditions. Consequently, no capillary suction occurs in the materials. This is modeled by setting $D_\theta = D_L = 0$.

All of the parameters needed to start the simulations are now determined. They will serve as input parameters to the preferred embodiment of the invention. The simulations are performed over a three-month period using 1080 time steps of two hours. The 12 mm disks are discretized with 50 elements. The latter all have the same length.

TABLE 3

Data for the numerical simulations - Second example

| Properties | Value | Properties | Value |
|---|---|---|---|
| Cement type | 10 | Cement composition | |
| w/c | 0.60 | $C_3S$ | 59.29 |
| | | $C_2S$ | 11.99 |
| | | $C_3A$ | 6.56 |
| | | $C_4AF$ | 9.13 |
| Concrete mixture | (kg/m$^3$) | Initial solid phases | (g/kg) |
| Cement | 1090.0 | C—S—H | 327.2 |
| Water | 654.0 | Portlandite | 185.4 |
| | | Ettringite | 104.5 |
| | | Hydrogarnet | 39.2 |
| Density | 1744.0 | | |
| Initial pore solution | (mmol/L) | Diffusion coefficients | (m$^2$/s) |
| OH$^-$ | 433.2 | OH$^-$ | $1.61 \times 10^{-10}$ |
| Na$^+$ | 111.1 | Na$^+$ | $4.07 \times 10^{-11}$ |
| K$^+$ | 327.0 | K$^+$ | $5.98 \times 10^{-11}$ |
| $SO_4^{2-}$ | 4.0 | $SO_4^{2-}$ | $3.25 \times 10^{-11}$ |
| Ca$^{2+}$ | 1.6 | Ca$^{2+}$ | $2.42 \times 10^{-11}$ |
| Al(OH)$_4^-$ | 0.07 | Al(OH)$_4^-$ | $1.62 \times 10^{-11}$ |
| Porosity | 0.522 | R | 8.3143 J/mol/° K |
| T | 25° C. | $\epsilon$ | $6.94 \times 10^{-10}$ C/V/m |
| F | 96488.46 C/mol | $\tau$ | 0.038 |
| $e_o$ | $1.602 \times 10^{19}$ C | | |

Results and Discussion

Figure 15:
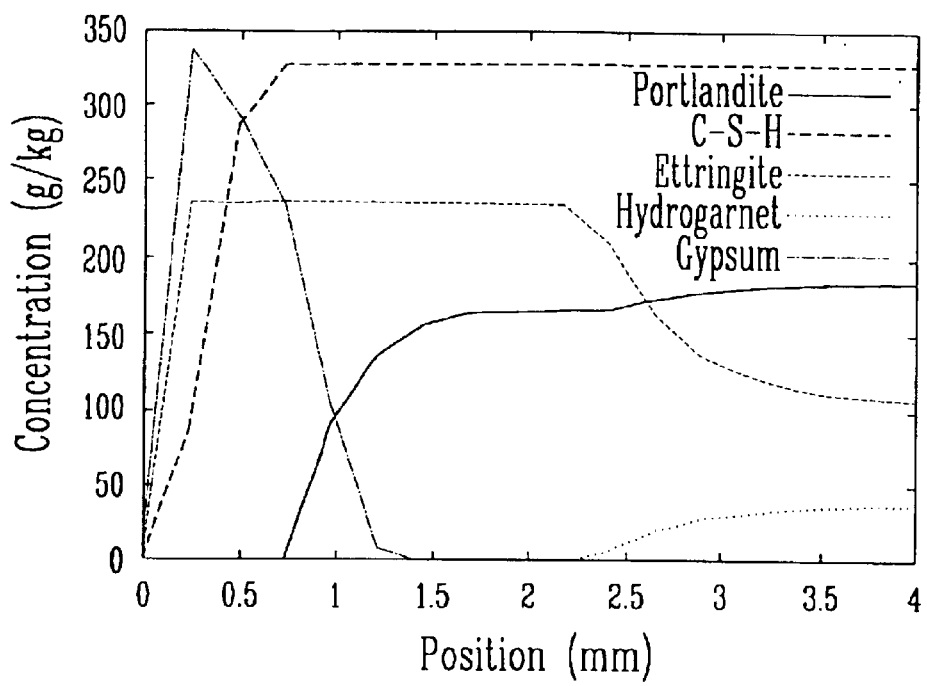
FIG. 15 is an illustration of the concentration (g/kg) versus the position (cm) for the solid phase distribution predicted by the model after 3 months of immersion in a 50 mmol/L $Na_2SO_4$ solution.

The invention predicts the spatial distribution of the various solid phases after a given period of exposure. The results for the 0.60 paste mixture immersed for 3 months in the sodium sulfate solution are summarized in FIG. 15. This ability of the model to predict the distribution of various solid phases should be of particular interest for those concerned by the consequences of chemical damage on the mechanical properties of the material. The precise knowledge of the solid phase distribution allows to calculate (at each location) the actual porosity of the material. These results could eventually be used to estimate the residual mechanical strength of the material.

The microprobe analysis gives profiles of total calcium and total sulphur content. To make comparisons with the results given by the invention, the total calcium content is calculated by considering the calcium found in portlandite, C—S—H, ettringite, hydrogarnet and gypsum. This gives the profile of FIG. 16. The same procedure is applied to sulphur, which is found in ettringite and gypsum. The result is shown in FIG. 17.

Figure 16:
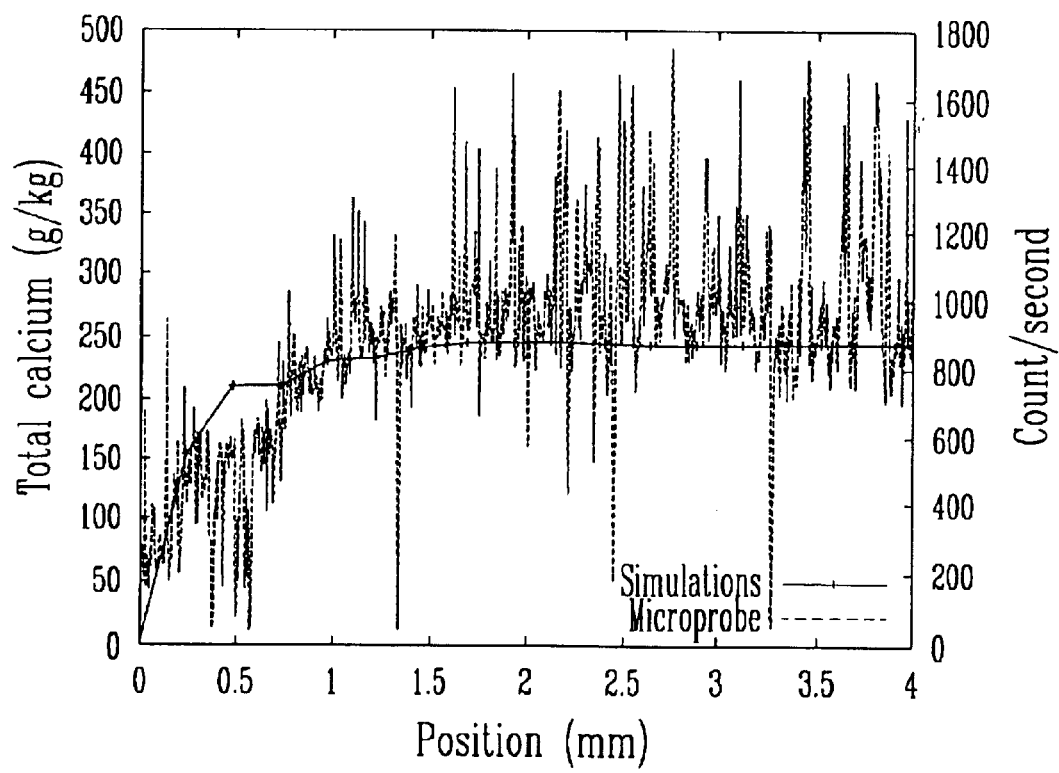
FIG. 16 is an illustration of the calcium profiles after 3 months immersed in 50 mmol/L $Na_2SO_4$ solution—The total calcium (g/kg) axis corresponds to the simulation and the count/second axis is associated to the microprobe data and both data sets are illustrated versus the position (mm)

As can be seen in FIG. 16, the algorithm of the preferred embodiment matches very well with the measured calcium profile. The invention can predict very accurately the beginning of the calcium loss, located at 1.3 mm from the surface. Toward the core of the sample (increasing x), no sign of degradation is apparent, which the model also reproduces. This is a very important result since the loss of calcium comes from the dissolution of portlandite and the decalcification of C—S—H, the two solid phases that give the material its strength. The invention can thus be used to predict the resistance loss of cementitious materials undergoing calcium leaching.

Figure 17:
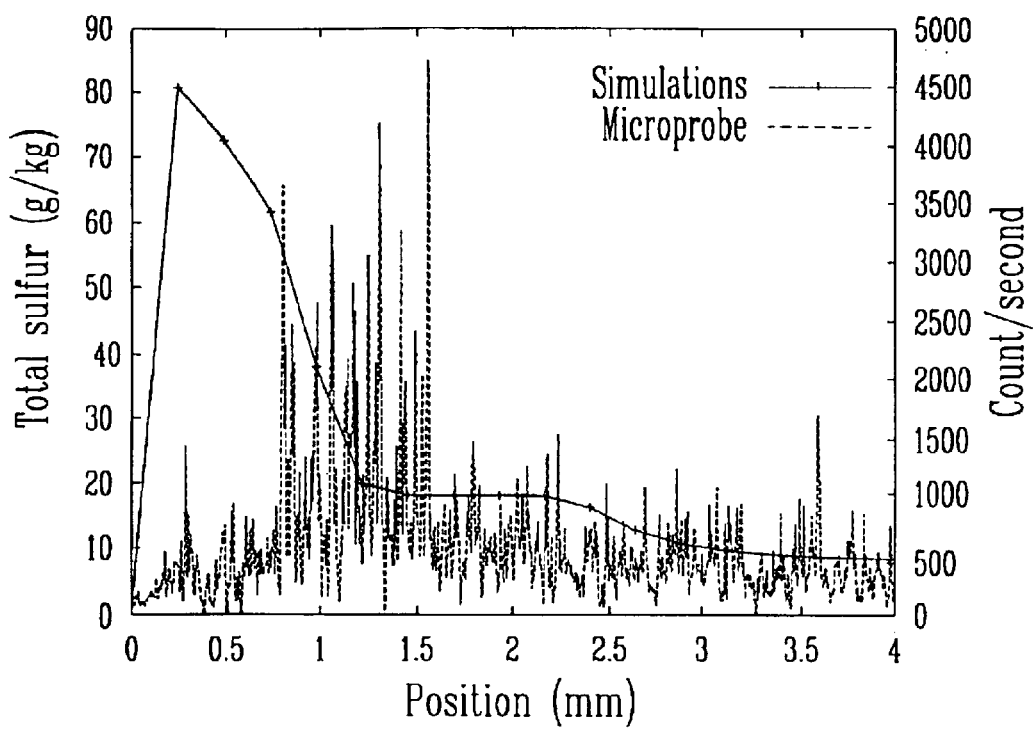
FIG. 17 is an illustration of the sulfur profile after 3 months immersed in 50 mmol/L $Na_2SO_4$ solution—The total sulfur (g/kg) axis corresponds to the simulation and the count/second axis is associated to the microprobe measurements.

Good results are also obtained with regard to the sulfur profile (FIG. 17). The microprobe analysis shows a slight increase in sulfur above the base level in the core of the sample at 2.2 mm. Not only does the model matches this increase but it gives information on the nature of this phenomenon. By comparing FIG. 17 with FIG. 15, one can see that it can be attributed to the penetration of an ettringite front.

The invention predicts a peak of sulfur near the surface of the material, also observed with the microprobe analysis. The comparison with FIG. 15 reveals that it is a peak of gypsum. There is a slight offset between the location of the peak measured with the microprobe and the one predicted by the model. The important amount of gypsum precipitated near the surface causes a very important reduction of the porosity in this region. Accordingly, the invention, through the damage factor G (see equation 20), reduces the diffusion coefficient of each ionic species. However, in the paste, the amount of gypsum is so important that it causes microcracking. This increases the transport properties instead of lowering them. It explains that the peak predicted by the model lags behind the one shown by the microprobe analysis.

It should be noted that the present invention can be carried out as a method, can be embodied in a system, a computer readable medium or an electrical or electromagnetical signal.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. A computer-implemented method for determining an ion concentration in solution of each of at least two ions capable of undergoing transport in a cement-based material under a chemical attack and a solid phase profile for at least one component of said cement-based material, said cement-based material having a solid skeleton and pores, said pores being at least one of liquid-filled and vapor-filled, a porosity of said cement-based material being provided, the method comprising the steps of:

determining a first concentration for each said at least two ions and an electrical potential profile using a transport algorithm, wherein the transport algorithm is a function of a diffusion of said at least two ions, of an adsorption of said at least two ions, of an electrical coupling between said at least two ions and a chemical activity of said at least two ions and wherein an ionic solution of said material is not in equilibrium with various solid phases of an hydrated paste of said cement-based material;

calculating a corrected concentration from said first concentration for each of said at least two ions and a first solid phase profile for each said at least one component using a chemical reactions algorithm, wherein at least one of a dissolution and a precipitation reactions is accounted for in order to maintain an equilibrium between said ionic solution and said various solid phases of said hydrated paste;

calculating a changed transport properties profile from said first solid phase profile to take into account an effect of said chemical reactions on said porosity of said material; and determining an ion concentration for each of said at least two ions and a solid phase profile for each of said at least one component using said changed transport properties profile, said corrected concentration and said first solid phase profile, wherein effects of said chemical reactions on an ionic transport are taken into account by correcting material transport properties whereby said ion concentration for each said at least two ions and said solid phase profile for each said at least one component in said cement-based material can be used to evaluate a degradation of said cement-based material.

2. A method as claimed in claim 1, wherein said step of calculating a first concentration comprises solving a set of equations.

3. A method as claimed in claim 2, wherein said set of equations is solved using a finite elements method.

4. A method as claimed in claim 1, further comprising a step of providing input data, said input data comprising a porosity, a temperature, ionic pore solution concentrations, an amount of each solid phase, a diffusion coefficient for each ionic species, a water diffusivity and an initial water content.

5. A method as claimed in claim 4, wherein said input data further comprises a finite element mesh and boundary conditions.

6. A method as claimed in claim 5, wherein said chemical reactions algorithm is performed on each node of said finite element mesh.

7. A method as claimed in claim 4, wherein said input data further comprises a number of time steps and a length of said time steps.

8. A method as claimed in claim 7, further comprising a step of determining a profile of said ion concentration by repeating said steps of determining a first concentration, calculating a corrected concentration, calculating a changed transport properties profile and determining an ion concentration and solid phase profile for each of said time steps.

9. A method as claimed in claim 1, further comprising a step of generating an indication of said ion concentration and an indication of said solid phase profile.

10. A method as claimed in claim 1, further comprising a step of determining a porosity profile using said solid phase profile, said ion concentration profiles and said electrical potential profile.

11. A method as claimed in claim 10, further comprising a step of generating an indication of said porosity profile.

12. A method as claimed in claim 1, wherein said components are at least one of C—S—H, Gypsum, Portlandite, Mirabilite, Ettringite and Hydrogarnet.

13. A method as claimed in claim 1, wherein said ions are at least one of $OH^-$, $Na^+$, $K^+$, $SO_4^{2-}$, $Ca^{2+}$ and $Al(OH)_4^-$.

14. A method as claimed in claim 1, wherein said step of determining a first concentration is carried out before said step of calculating a corrected concentration.

15. A method as claimed in claim 1, wherein said transport algorithm is further a function of a capillary suction, said capillary suction arising when said material is exposed to a gradient of relative humidity, said transport algorithm thereby determining a water content profile.

16. A method as claimed in claim 15, further comprising a step of providing input data, said input data comprising a porosity, a temperature, ionic pore solution concentrations, an amount of each solid phase, a diffusion coefficient for each ionic species, a water diffusivity and an initial water content.

17. A method as claimed in claim 16, wherein said input data further comprises a number of time steps and a length of said time steps.

18. A method as claimed in claim 17, further comprising a step of determining a profile of said ion concentration by repeating said steps of determining a first concentration, calculating a corrected concentration, calculating a changed transport properties profile and determining an ion concentration and solid phase profile for each of said time steps.

19. A computer-implemented method for determining a diffusion coefficient for each of at least two ions capable of undergoing transport in a cement-based material, said cement-based material having a solid skeleton and pores, said pores being at least one of liquid-filled and vapor-filled, a porosity of said cement-based material being provided, the method comprising the steps of:

determining a concentration for each said at least two ions and an electrical potential profile using a transport algorithm, wherein the transport algorithm is a function of a diffusion of said at least two ions, of an electrical coupling between said at least two ions and a chemical activity of each said at least two ions and wherein said electrical coupling is solved using a Poisson equation;

determining an electrical current using said concentration and said electrical potential profile; and determining a diffusion coefficient for each of at least two ions using said electrical current.

20. A method as claimed in claim 19, further comprising:

providing input data, said input data comprising a set of tortuosity parameters and a measured electrical current for said material, and determining a diffusion coefficient for each of said ions by calculating a set of electrical currents each electrical current corresponding to one of said tortuosity parameter in said set of tortuosity parameters using said concentration, said electrical potential and each one of said tortuosity parameter in said set of tortuosity parameters;

choosing an electrical current from said set with a value closest to said measured electrical current;

determining a matching tortuosity parameter corresponding to said chosen electrical current; and determining said diffusion coefficient for each of said ions using said matching tortuosity.

* * * * *